(12) United States Patent
Longoria

(10) Patent No.: US 10,398,498 B2
(45) Date of Patent: Sep. 3, 2019

(54) TISSUE ABLATION DEVICES AND METHODS OF USING THE SAME

(71) Applicant: LC Therapeutics Inc., Sacramento, CA (US)

(72) Inventor: James Longoria, Sacramento, CA (US)

(73) Assignee: LC Therapeutics, Inc., Sacramento, CA (US)

( * ) Notice: Subject to any disclaimer, the term of this patent is extended or adjusted under 35 U.S.C. 154(b) by 306 days.

(21) Appl. No.: 15/228,425

(22) Filed: Aug. 4, 2016

(65) Prior Publication Data
US 2017/0035492 A1 Feb. 9, 2017

Related U.S. Application Data

(60) Provisional application No. 62/201,013, filed on Aug. 4, 2015, provisional application No. 62/387,435, filed on Dec. 23, 2015.

(51) Int. Cl.
*A61B 18/14* (2006.01)
*A61B 18/08* (2006.01)
*A61B 18/00* (2006.01)

(52) U.S. Cl.
CPC ........ *A61B 18/1445* (2013.01); *A61B 18/085* (2013.01); *A61B 18/1482* (2013.01); *A61B 2018/00178* (2013.01); *A61B 2018/00577* (2013.01)

(58) Field of Classification Search
CPC ..... A61B 18/08; A61B 18/082; A61B 18/085; A61B 18/1442; A61B 18/1445; A61B 2018/1465; A61B 17/28; A61B 17/282; A61B 17/29; A61B 2017/2926; A61B 2017/2945; A61B 18/1482; A61B 2018/00178; A61B 2018/00577
See application file for complete search history.

(56) References Cited

U.S. PATENT DOCUMENTS

| | | | |
|---|---|---|---|
| 6,113,598 | A | 9/2000 | Baker |
| 6,770,072 | B1 | 8/2004 | Truckai et al. |
| 7,169,146 | B2 | 1/2007 | Truckai et al. |
| 7,189,233 | B2 | 3/2007 | Truckai et al. |
| 7,309,849 | B2 | 12/2007 | Truckai et al. |
| 7,381,209 | B2 | 6/2008 | Truckai et al. |

(Continued)

OTHER PUBLICATIONS

Brutchey et al., Positive Temperature Coefficient of Resistivity in Donor-Doped BaTiO3 Ceramics Derived from Nano-Crystals Synthesized at Low Temperature, Adv. Mater. (2008), 20:1029-1033.

*Primary Examiner* — Michael F Peffley
(74) *Attorney, Agent, or Firm* — Rogowski Law LLC

(57) ABSTRACT

Tissue ablation devices are provided. Aspects of the tissue ablation devices include an elongated member having a proximal and distal end. At the distal end are first and second jaws that are configured to apply ablation energy to tissue disposed between the jaws during use. Each jaw includes a surface proximal radiofrequency (RF) ablation energy component and a surface distal thermal ablation energy component. Also provided are systems that include a tissue ablation device operatively coupled to an energy source, as well as kits that include the devices and methods of using the devices in tissue ablation applications, including cardiac tissue ablation applications.

18 Claims, 20 Drawing Sheets

(56) References Cited

U.S. PATENT DOCUMENTS

| | | | |
|---|---|---|---|
| 7,951,147 B2* | 5/2011 | Privitera | A61B 18/1445 606/205 |
| 7,981,113 B2 | 7/2011 | Truckai et al. | |
| 2005/0033282 A1 | 2/2005 | Hooven | |
| 2005/0072827 A1 | 4/2005 | Mollenauer | |
| 2006/0217699 A1 | 9/2006 | Wang | |
| 2008/0172048 A1* | 7/2008 | Martin | A61B 18/1442 606/10 |
| 2009/0076506 A1 | 3/2009 | Baker | |
| 2010/0036370 A1 | 2/2010 | Mirel et al. | |
| 2010/0185186 A1 | 7/2010 | Longoria | |
| 2011/0166563 A1* | 7/2011 | Cheng | A61B 18/082 606/30 |
| 2013/0317492 A1 | 11/2013 | Truckai et al. | |
| 2013/0334280 A1* | 12/2013 | Krehel | A61B 17/07207 227/176.1 |
| 2014/0214019 A1 | 7/2014 | Baxter, III et al. | |
| 2015/0032094 A1* | 1/2015 | Kane | A61B 18/18 606/33 |
| 2015/0141993 A1* | 5/2015 | Schechter | A61B 18/1445 606/51 |
| 2015/0366607 A1* | 12/2015 | Bek | A61B 18/1485 606/41 |
| 2016/0015448 A1 | 1/2016 | Longoria et al. | |

* cited by examiner

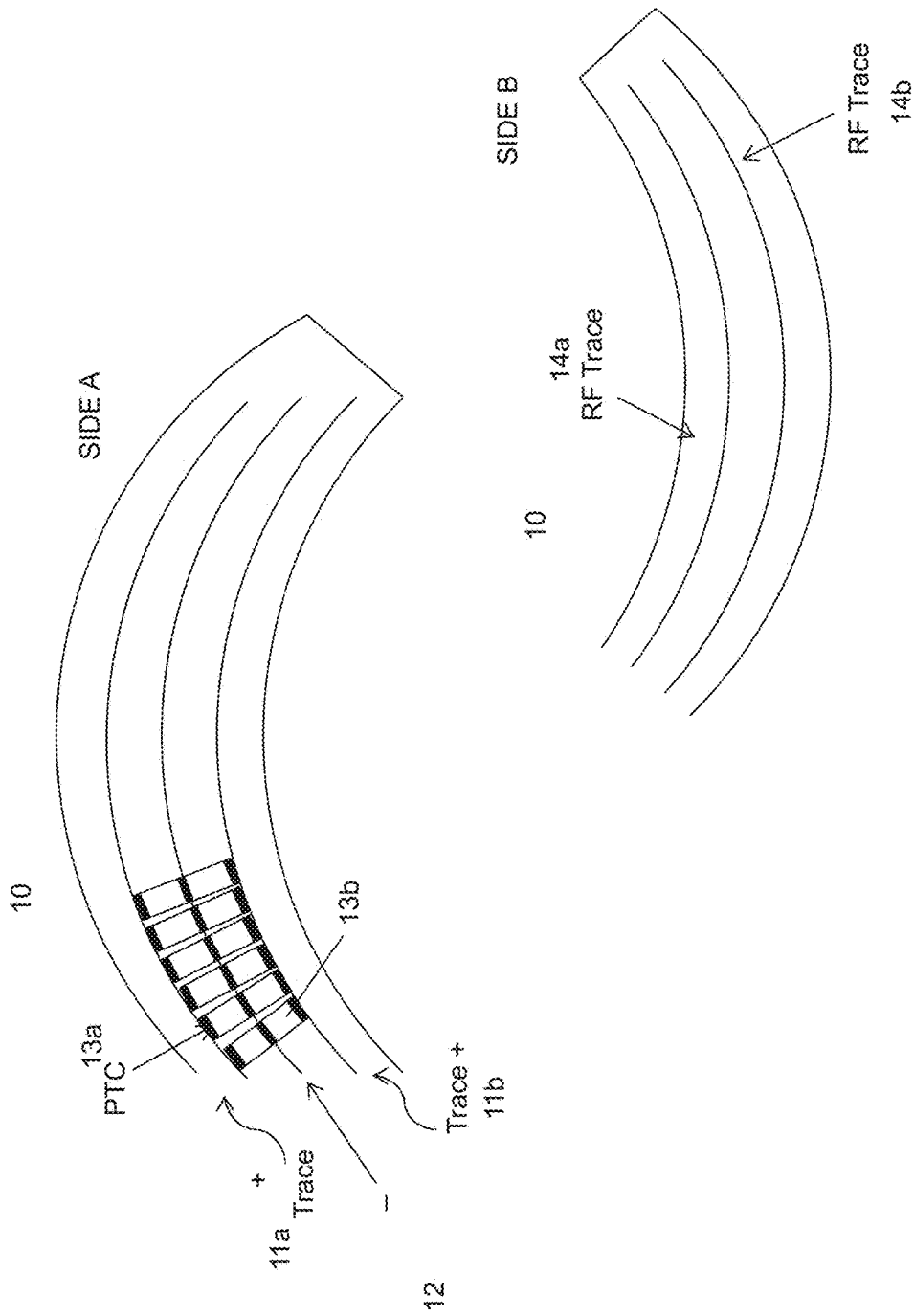

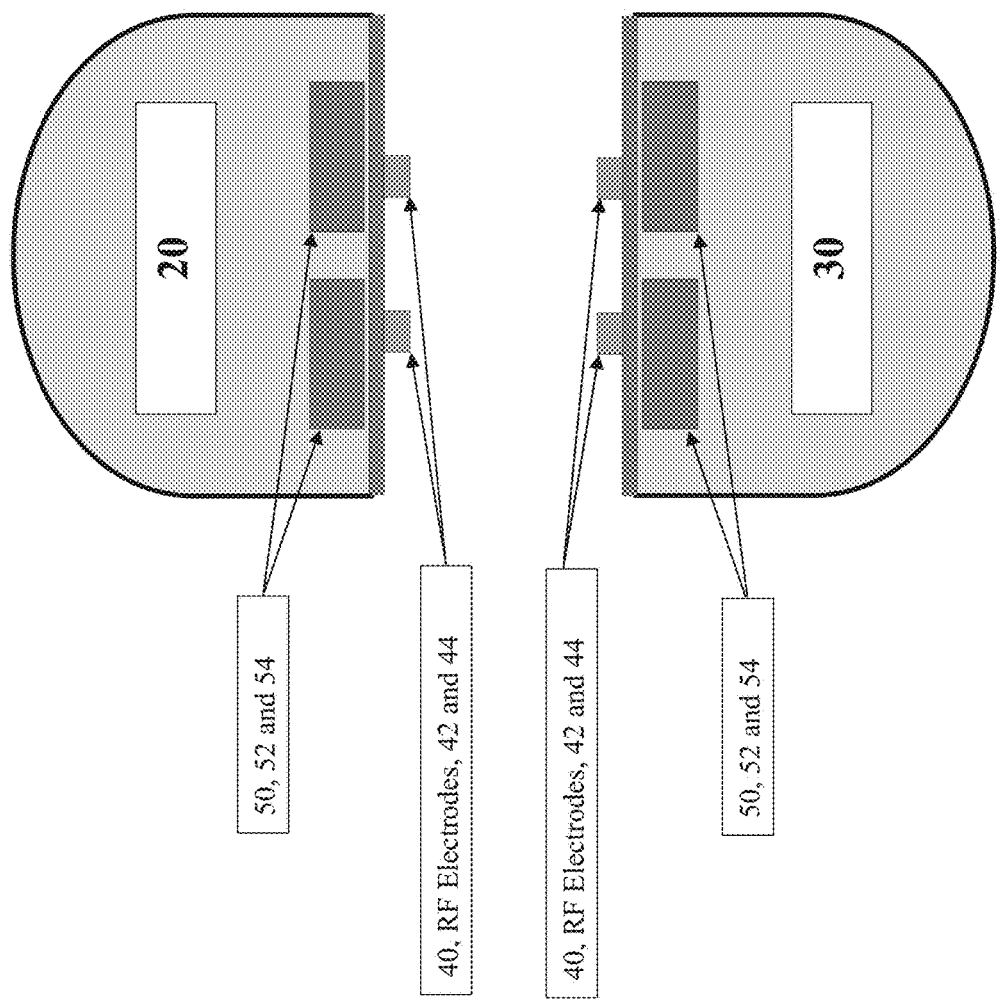

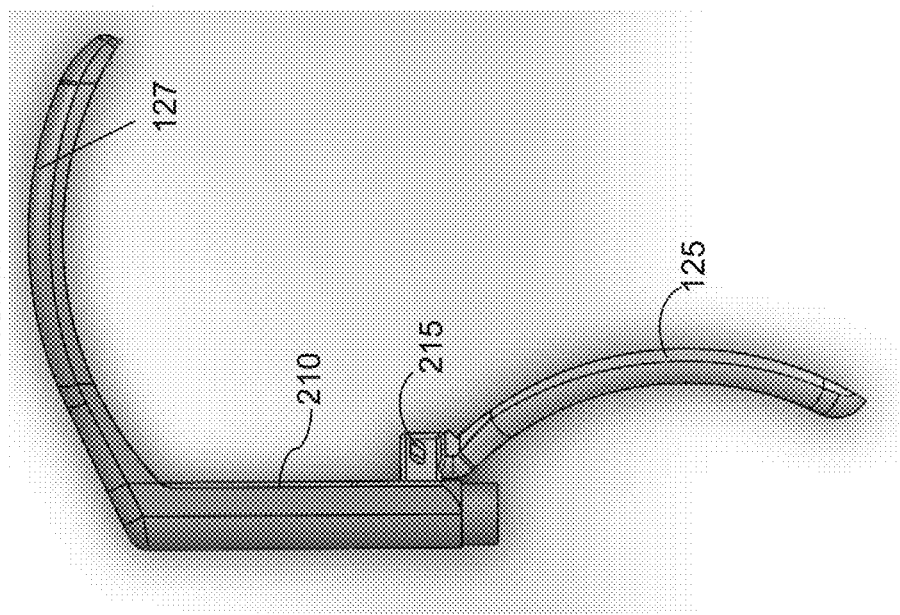

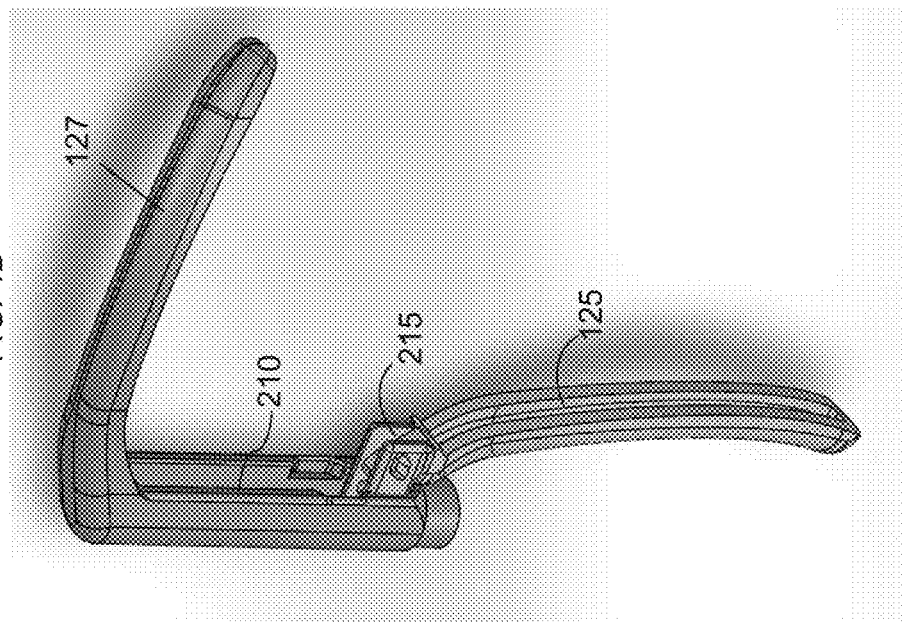

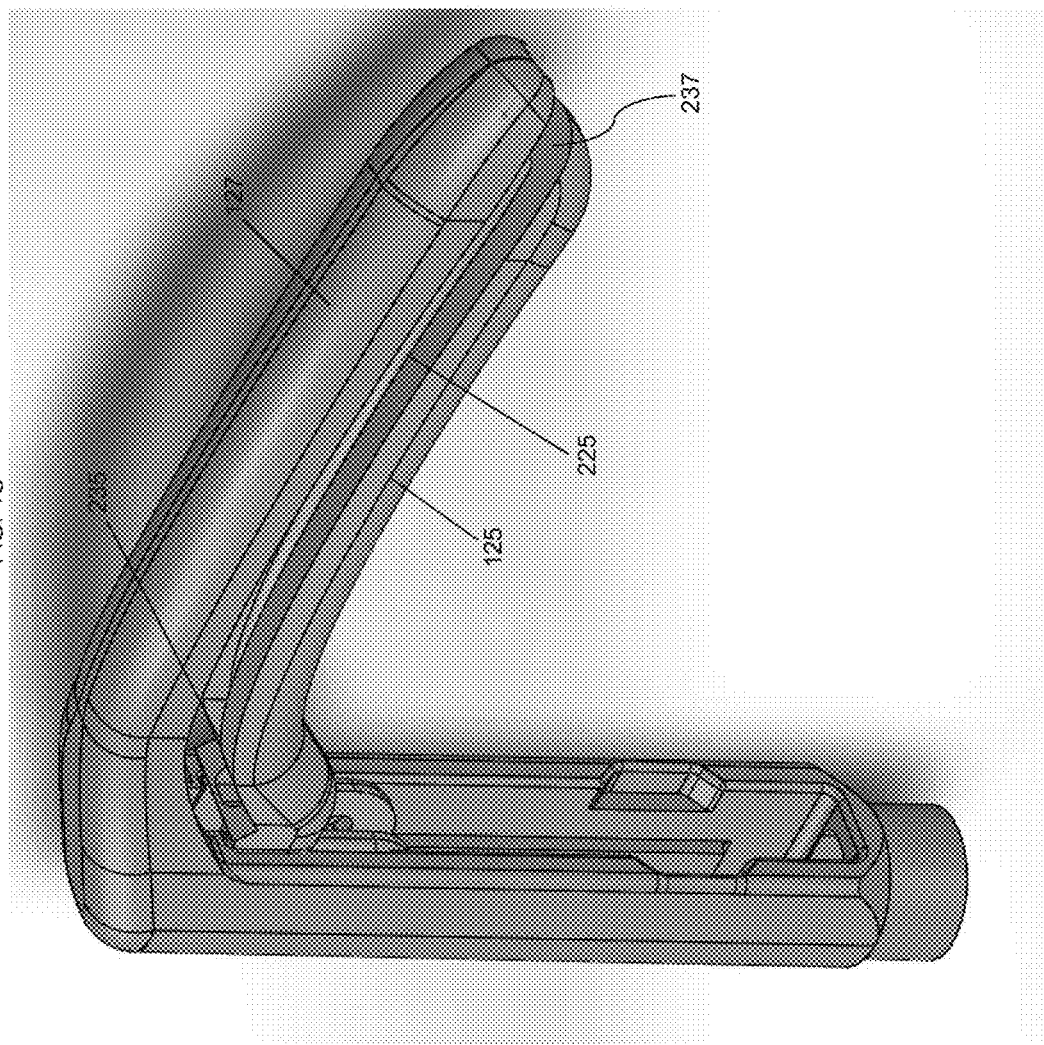

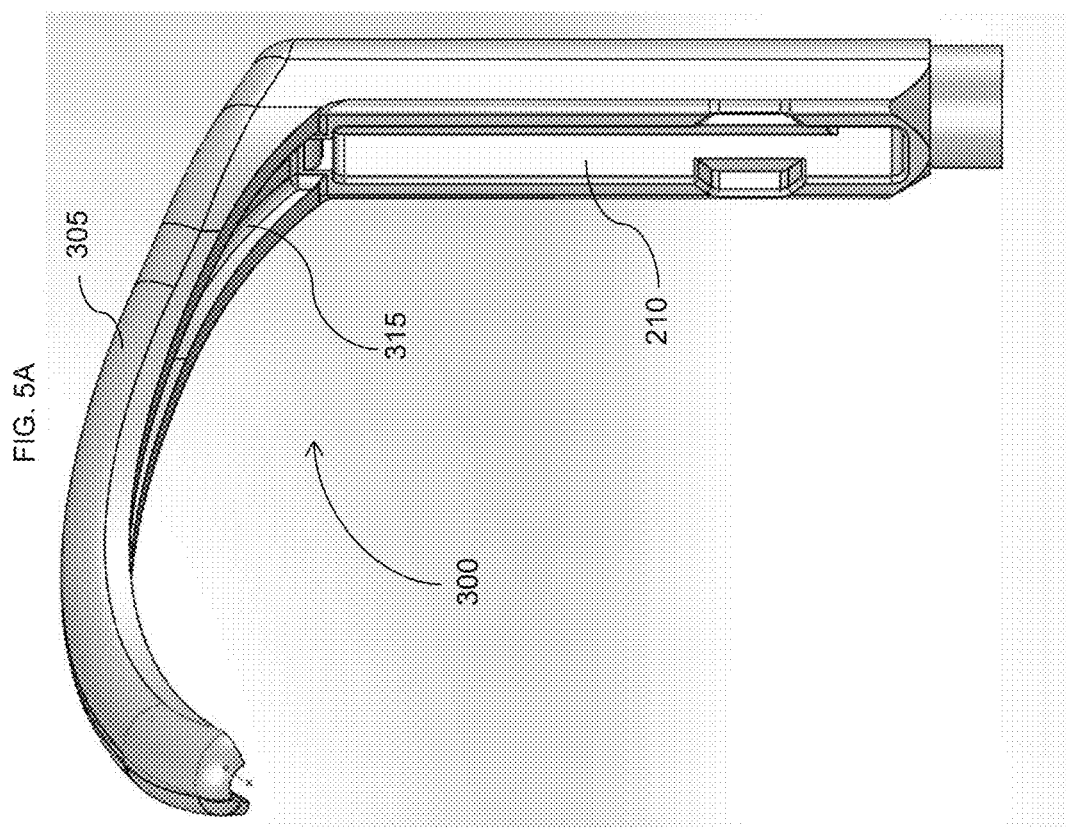

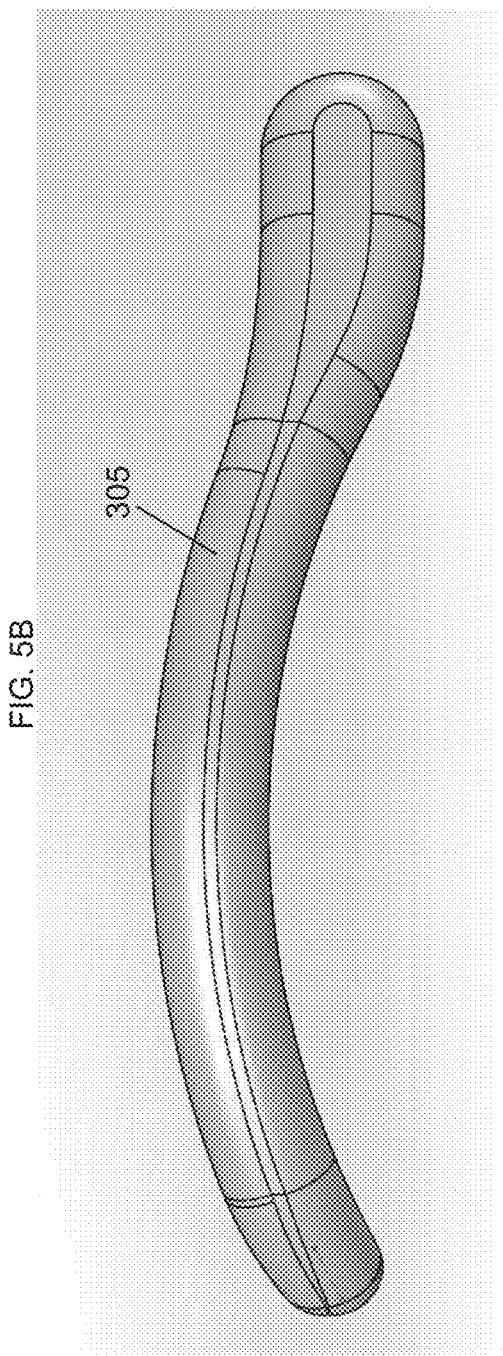

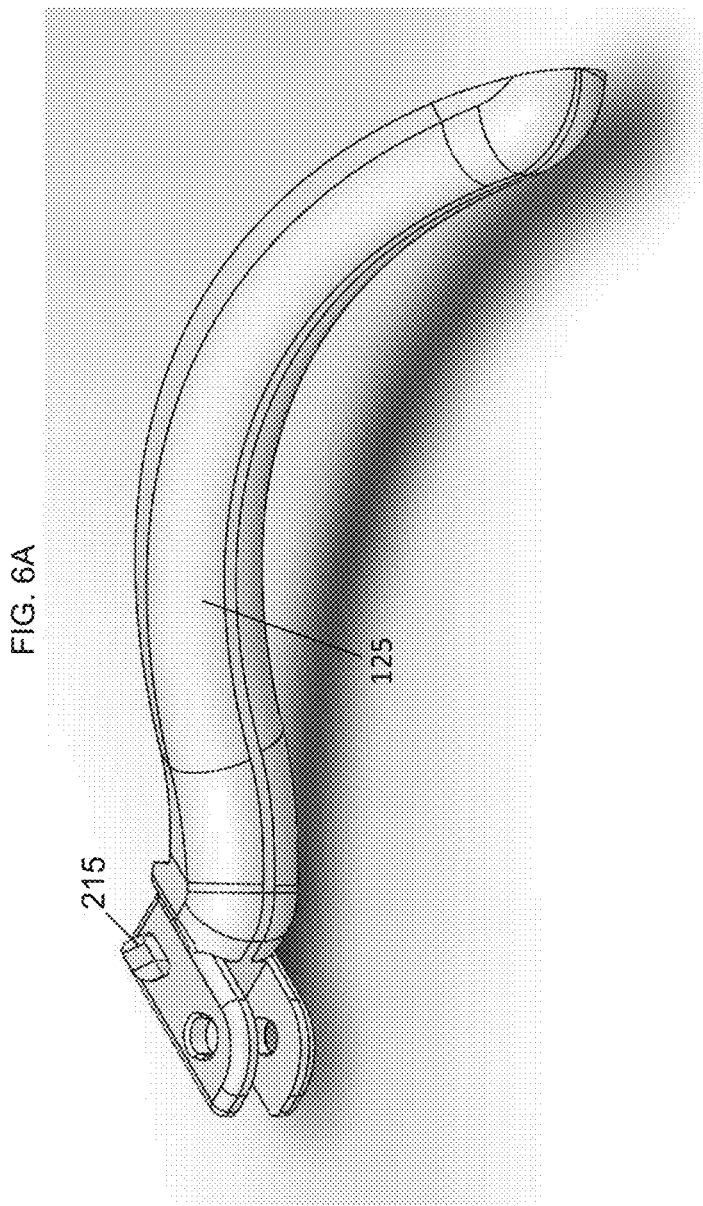

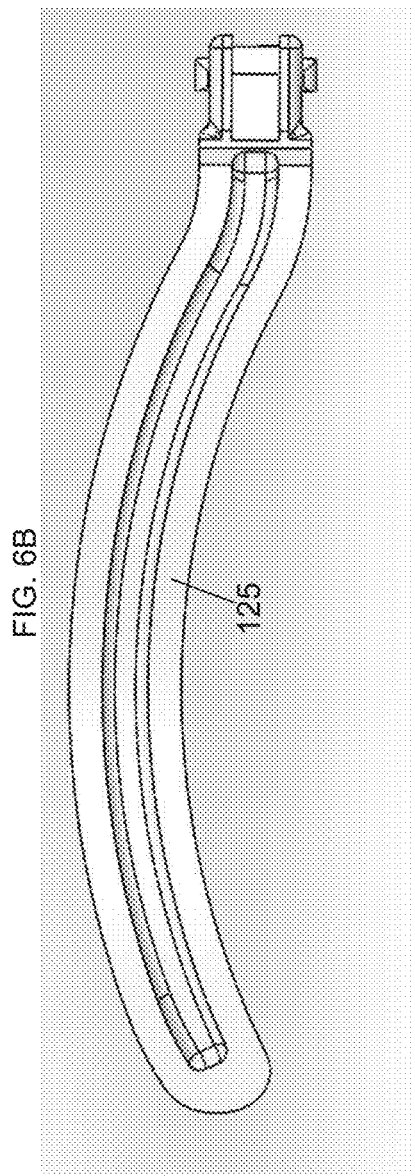

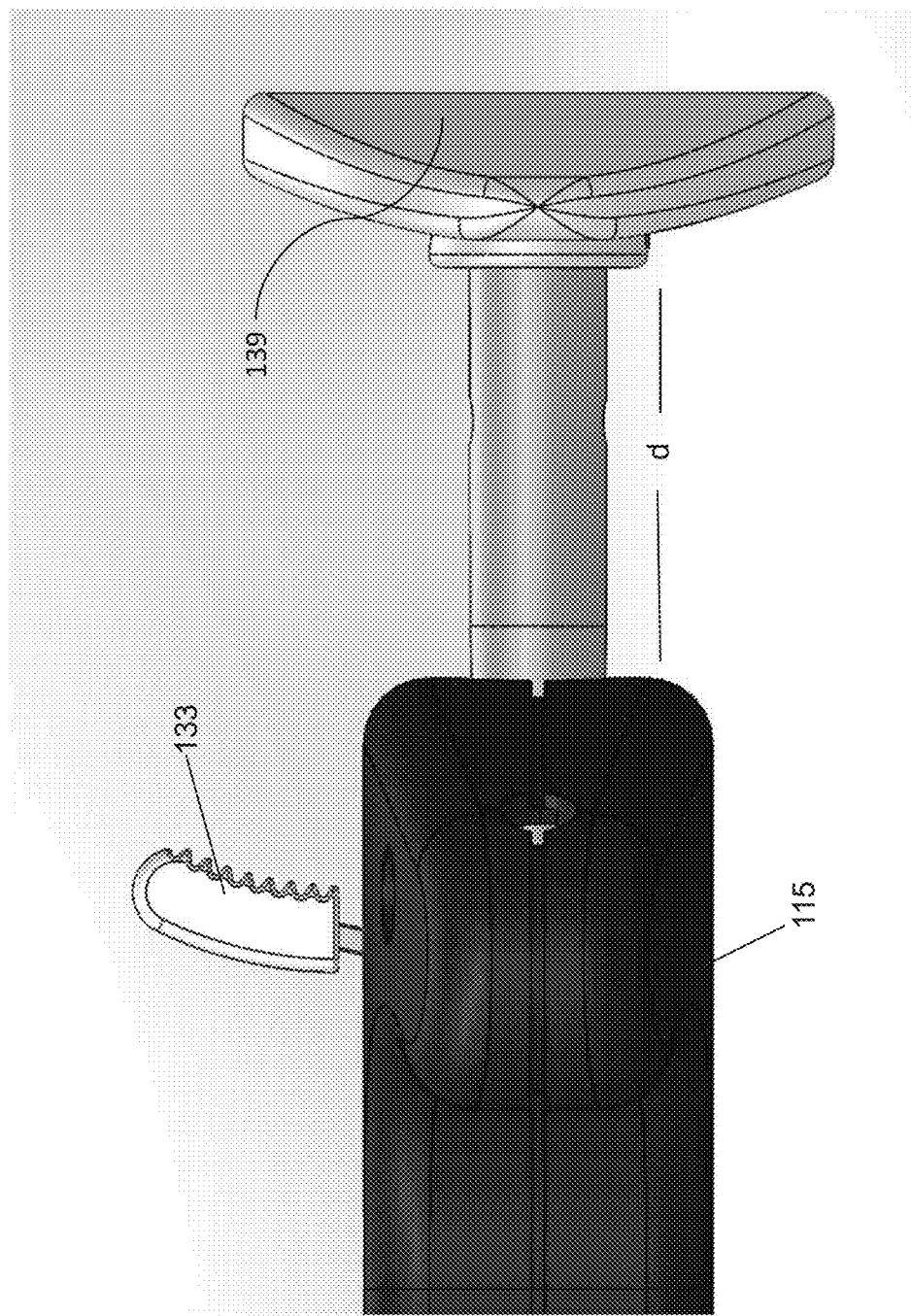

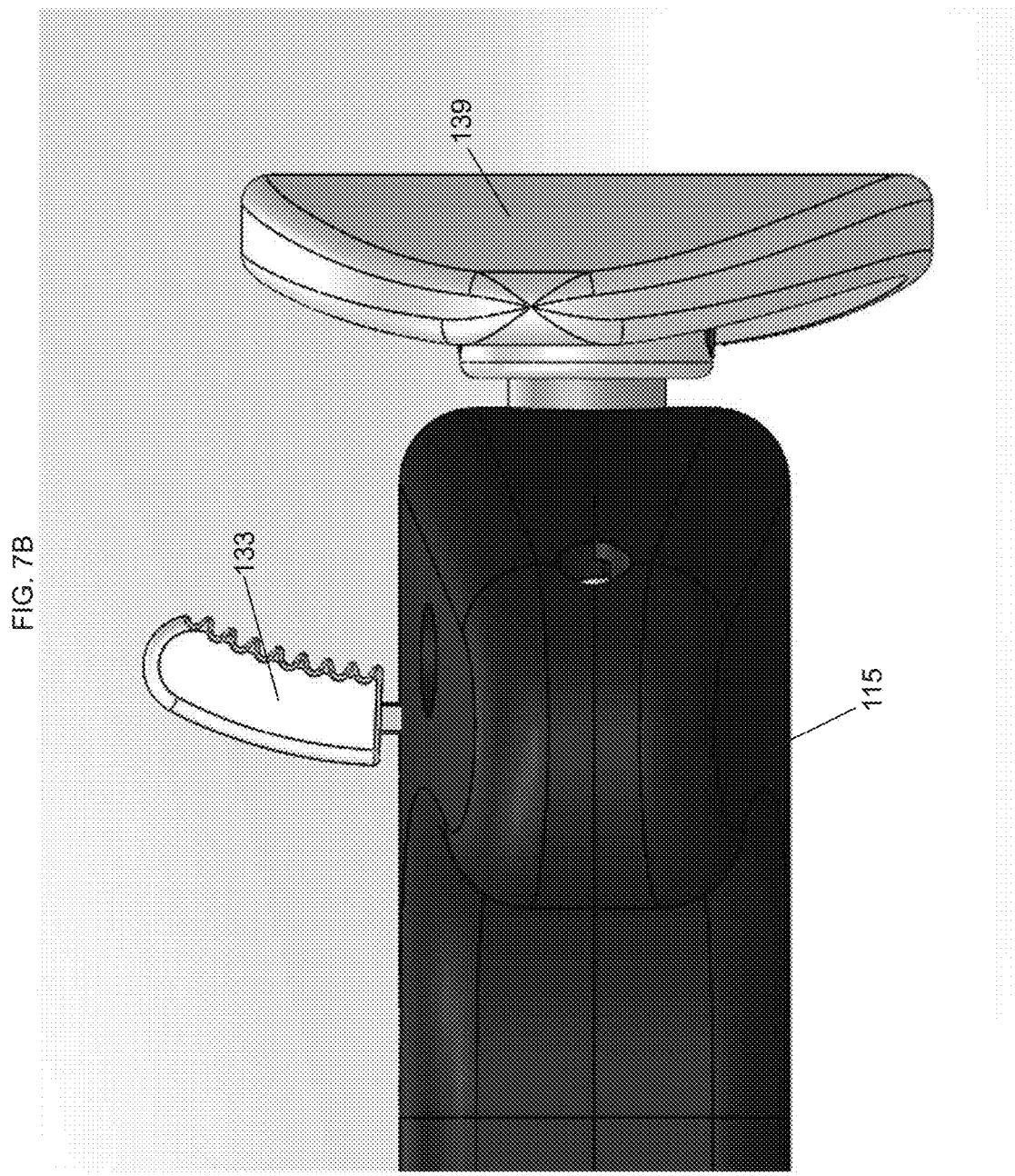

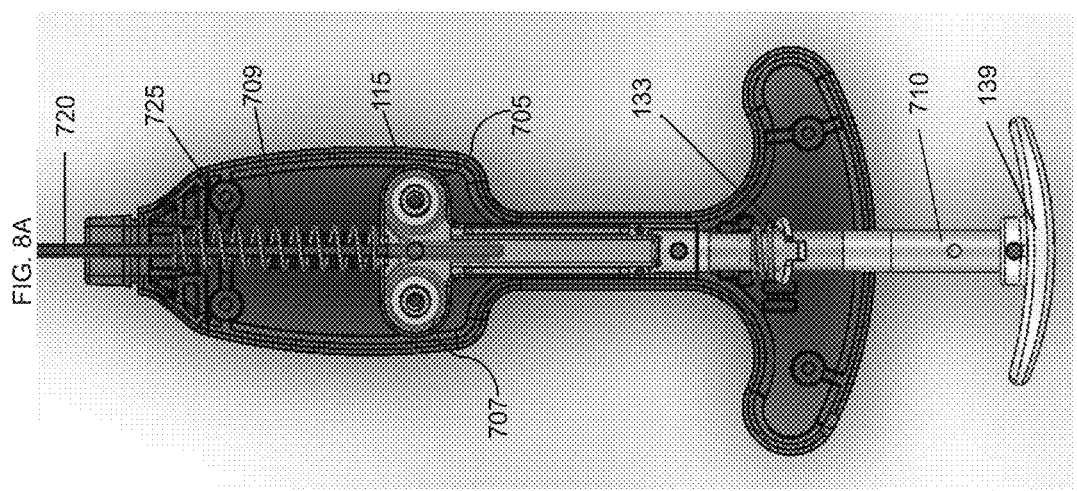

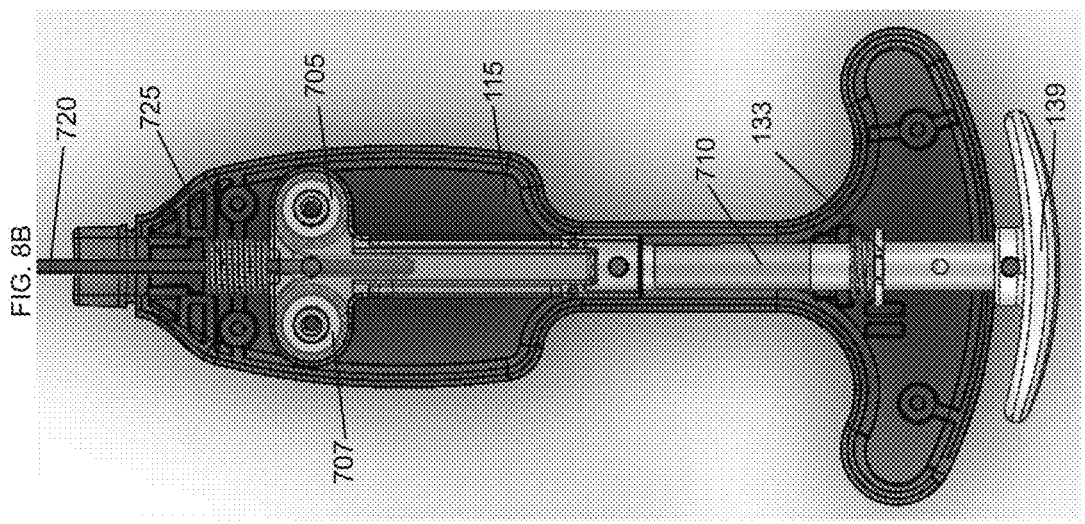

TISSUE ABLATION DEVICES AND METHODS OF USING THE SAME

CROSS-REFERENCE TO RELATED APPLICATIONS

Pursuant to 35 U.S.C. § 119 (e), this application claims priority to the filing date of the U.S. Provisional Patent Application Ser. No. 62/201,013 filed Aug. 4, 2015 and to the filing date of the U.S. Provisional Patent Application Ser. No. 62/387,435 filed Dec. 23, 2015; the disclosures of which applications are herein incorporated by reference.

INTRODUCTION

In medicine, ablation therapy includes procedures used to target, destroy or remove tissue. Ablation therapies exist for a variety of conditions. Several ablation therapies exist for heart conditions and may be performed surgically or through minimally invasive procedures. For example, ablation is used to treat conditions of the heart, where such conditions include irregular heart rhythms and abnormal signal conduction. Cardiac ablation may treat several paroxysmal, persistent, or longstanding heart arrhythmias including those afflicting the upper (atria) or lower (ventricles) chambers of the heart. Atrial or atrioventricular heart rhythm disorders include supraventricular tachycardia conditions such as Wolff-Parkinson-White syndrome, atrioventricular or AV nodal re-entrant tachycardia, atrial tachycardia, atrial flutter, sinus tachycardia, and atrial fibrillation. Ventricular arrhythmias amenable to ablation include ventricular tachycardia and certain cases of ventricular fibrillation.

Ablation therapy may be achieved with lasers, injection of chemical agents, heat and energy generated by radio frequency waves or microwaves, focused ultrasound or freezing by cryoablation. Ablation therapy may be performed with a variety of different types of devices, including thin probes, catheters, or energy beams to target specific problematic areas in the body. Minimally invasive variations of cardiac ablation are carried out with catheters, probes and endoscopes inserted into small incisions or blood vessels in the groin, arm, chest or neck. The heart does not need to be stopped nor does the chest cavity need to be opened. Radiofrequency catheters, microwave catheters, and lasers direct heat and energy to carefully cauterize small areas of heart tissue. The four major types of radiofrequency ablation catheters are standard 4 mm tip catheters, 8-10 mm tip catheters, open-loop irrigated tip catheters, and closed-loop irrigated tip catheters (Mussigbrodt, et al., "Irrigated Tip Catheters for Radiofrequency Ablation in Ventricular Tachycardia," BioMed Research International (2015) 2015).

SUMMARY

Tissue ablation devices are provided. Aspects of the tissue ablation devices include an elongated member having a proximal and distal end. At the distal end are first and second jaws that are configured to apply ablation energy to tissue disposed between the jaws during use. Each jaw includes a surface proximal radiofrequency (RF) ablation energy component and a surface distal thermal ablation energy component. Also provided are systems that include a tissue ablation device operatively coupled to an energy source, as well as kits that include the devices and methods of using the devices in tissue ablation applications, including cardiac tissue ablation applications.

BRIEF DESCRIPTION OF THE FIGURES

FIGS. 1A and 1B provide schematic representations of flex circuits having surface proximal RF ablation energy electrodes and surface distal thermal ablation energy electrodes, according to embodiments of the invention.

FIGS. 2A to 2D provide various views of jaws that include the flex circuit of FIG. 1A.

FIGS. 4A to 4C provide views of the proximal and distal jaws at the proximal end of the device shown in FIGS. 3A and 3B.

FIGS. 5A and 5B provide different views of the jaw housing of the distal jaw of the device shown in FIGS. 3A and 3B.

FIGS. 6A and 6B provide different views of the proximal jaw of the device shown in FIGS. 3A and 3B.

FIGS. 7A and 7B provide views of the handle of the ablation device of FIGS. 3A and 3B in an un-deployed and deployed state, respectively.

FIGS. 8A and 8B provide views of the inside of a handle of the ablation device of FIGS. 3A and 3B in an un-deployed and deployed state, respectively.

DETAILED DESCRIPTION

Figure 1A:
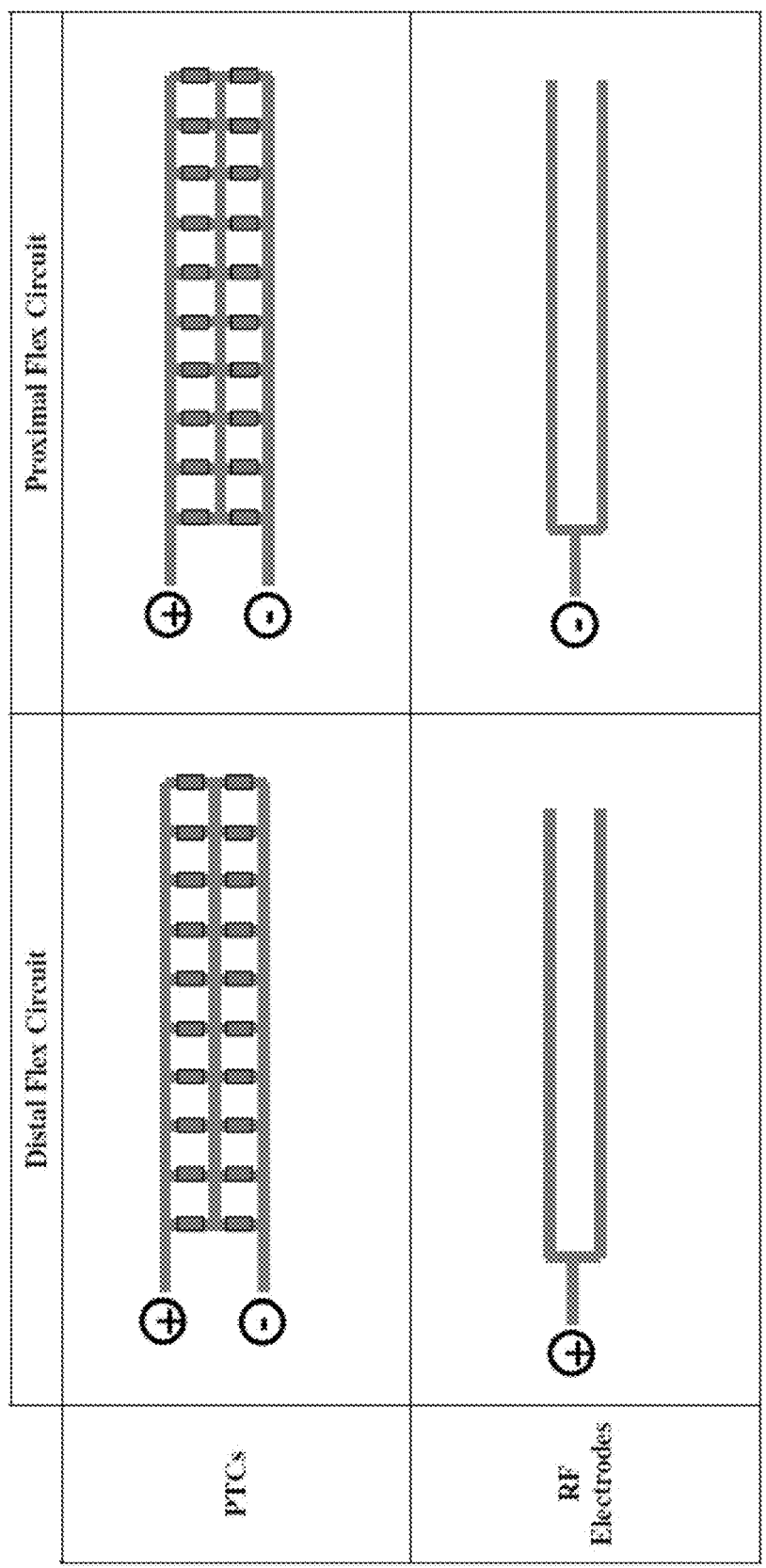

Tissue ablation devices are provided. Aspects of the tissue ablation devices include an elongated member having a proximal and distal end. At the distal end are first and second jaws that are configured to apply ablation energy to tissue disposed between the jaws during use. Each jaw includes a surface proximal radiofrequency (RF) ablation energy component and a surface distal thermal ablation energy component. Also provided are systems that include a tissue ablation device operatively coupled to an energy source, as well as kits that include the devices and methods of using the devices in tissue ablation applications, including cardiac tissue ablation applications.

Before the methods of the present disclosure are described in greater detail, it is to be understood that the methods of the present disclosure are not limited to particular embodiments described, as such may, of course, vary. It is also to be understood that the terminology used herein is for the purpose of describing particular embodiments only, and is not intended to be limiting, since the scope of the methods of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present disclosure. The upper and lower limits of these smaller ranges may independently be included in the smaller ranges and are also encompassed within the present disclosure, subject to any specifically excluded limit in the stated range. Where the stated range includes one or both of the limits, ranges excluding either or both of those included limits are also included in the present disclosure.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the present disclosure belongs. Although any methods and materials similar or equivalent to those described herein can also be used in the practice or testing of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

Devices

As summarized above, aspects of the invention include tissue ablation devices. By tissue ablation device is meant a device that is configured to ablate tissue, e.g., soft tissue, in a living subject, e.g., a mammal, such as a human. The term "ablate" is used in its conventional sense to refer to the removal or destruction of the function of the target tissue. As the devices are configured to ablate tissue, they are configured to remove or destroy the function of targeted tissue. Tissue ablation devices of the invention include devices that are configured to apply radiofrequency (RF) and/or thermal ablative energy to a tissue location of a living organism. As such, in some instances the ablation energy delivered to soft tissue by the devices is at least one of RF ablative energy (i.e., RF energy) and thermal ablative energy (i.e., thermal energy). By RF ablative energy is meant an alternating current of sufficiently high frequency to ablate target tissue, e.g., by heating the target tissue. In some instances, the devices are configured to apply by RF and thermal ablation energy. While the frequency employed in a given RF tissue ablation procedure may vary, in some instances the RF ablative energy applied by devices described herein ranges from 250 to 1000 kHz, such as from 300 to 600 kHz, including from 350 to 500 kHz, e.g., from 400 to 500 kHz, at a power level sufficient to raise the target tissue to a sufficiently high temperature for a time sufficient to result in the desired tissue ablation. In some instances, the tissue temperature that is achieved when RF ablative energy is applied to target tissue using the devices described herein is 45° C. or greater, such as 50° C., and in some instances is 105° C. or less, such as 95° C. or less. In addition to, or instead of (as described in greater detail below), the devices may be configured to apply non-RF thermal ablative energy to target soft tissue. In some instances, the tissue temperature that is achieved when such non-RF thermal ablative energy is applied to target tissue using the devices described herein is 45° C. or greater, such as 50° C., and in some instances is 105° C. or less, such as 95° C. or less. The devices are configured to apply the ablative energy to target tissue for a period of time sufficient to achieve the desired target tissue ablation, and in some instances are configured to apply the ablative energy to target tissue for a period of time ranging from 10 to 90 seconds, such as 30 to 60 seconds.

Aspects of the devices include an elongated member having proximal and distal ends, with first and second jaws being positioned at the distal end. While the dimensions of the elongated member may vary widely depending on the particular application for which the device is designed, in some instances the elongated member may have a length ranging from 1 to 100 cm, such as 5 to 50 cm and including 10 to 35 cm. The cross sectional shape of the elongated member may vary, ranging from circular to oval to rectangular, e.g., square, to triangular, or other convenient shape as desired, where the shape may be the same or different along the length of the elongated member. The longest cross sectional dimension, e.g., outer diameter, of the elongated member may also vary, and in some instances may range from 0.1 to 2 cm, such as 0.5 to 1.5 cm and including 0.75 to 1.25 cm. The elongated member may include one or more internal passageways, e.g., for electrode connectors, e.g., cables, actuator rods for articulated jaws, etc., for operably connecting the distal end elements (e.g., jaws, electrodes, illumination element, etc.) to control elements which may be located at the proximal end. The elongated member may be rigid, and may be fabricated from a variety of different materials, where such materials include, but are not limited to: polymeric materials, e.g., plastics, metals, e.g., stainless steel, and the like. In some instances, the elongated member includes a bend positioned between the proximal and distal ends. When present, the angle of the bend may vary, and in some instances ranges from 5 to 50, such as 10 to 30, e.g., 15°.

Positioned at the distal end of the elongated member are first and second jaws, which jaws are configured to apply ablative energy to soft tissue disposed between the jaws during use. By "positioned at the distal end" is meant that the first and second jaws are located at least near the distal end of the elongated member, and in some instances within 10 cm or less of the distal end, such as 5 cm or less of the distal. As such, the first and second jaws may be located at the distal end, e.g., where the device has a rongeur configuration, or at least near the actual distal end of the device, e.g., where the device has a clamp configuration. The first and second jaws may be referred to as proximal and distal jaws, with the proximal jaw being the jaw closest to the proximal end of the device and the distal jaw being the jaw furthest away from the proximal end of the device.

The first and second jaws are dimensioned to provide for the desired tissue to be positioned therebetween during use in a manner sufficient to achieve the desired tissue ablation.

The tissue contact area of the jaws, i.e., that portion of each jaw which is configured to contact tissue during use, may be the same or different. While the tissue contact area of each jaw may vary, in some instances the tissue contact area ranges from 0.1 to 10 cm², such as 0.5 to 5 cm². The tissue contact area of each jaw may be planar or non-planar, as desired. Furthermore, the tissue contact area may be smooth or textured, as desired. The jaws may have a length that varies, ranging in some instances from 0.5 to 5 cm, such as 0.75 to 4 cm and including 1 to 2.5 cm. The width of the jaws may also vary, ranging in some instances from 0.1 to 2.5 cm, such as 0.25 to 1 cm and including 0.25 to 0.75 cm. The first and second jaws may be fabricated from any convenient material, e.g., polymeric materials, e.g., plastics such as ABS, polycarbonate, PEEK, Ultem, etc., metals, e.g., stainless steel, and the like.

In some instances, the first and second jaws (i.e., proximal and distal jaws) are configured to apply intra and inter ablative energy to tissue disposed between the jaws during use. Intra ablative energy is ablative energy that does not pass through target tissue disposed between the first and second jaws, while inter ablative energy is energy that passes through target tissue disposed between the first and second jaws. In other words, intra ablative energy is energy that does not traverse the target tissue, while inter ablative energy is energy that traverses the target tissue. Where the target tissue positioned between the first and second jaws during use can be described as being a target tissue made up of one or more walls, e.g., where target tissue is cardiac tissue clamped between the first and second jaws during a cardiac ablation procedure (such as described in greater detail below), inter ablative energy may also be characterized as transmural ablative energy, while intra ablative energy is non-transmural energy.

Aspects of the invention include devices where one or both of the jaws includes a surface proximal radiofrequency (RF) ablation energy component and a surface distal thermal ablation energy component. During use, the surface proximal RF ablation energy component is closest to the tissue contacting surface of the jaw, i.e., is nearest to the tissue relative to the thermal ablation component. Furthermore, the surface distal thermal ablation energy component is furthest from the tissue contacting surface of the jaw, i.e., is furthest from the tissue relative to the RF ablation component. In some instances, tissue contacting surface of the jaw includes the RF ablation component and the thermal ablation component is present in the jaw, e.g., behind the RF ablation component. Viewed another way, the disparate components may be aligned from the tissue contacting surface of the jaw to the interior of the jaw in the order of the RF ablation element and then the thermal ablation element.

In some instances, the RF ablation energy component includes at least one elongated electrode, such as one or more, e.g., two or more, elongated electrodes. The elongate electrode(s) may span the length of the tissue contact area of each jaw, or just a portion thereof. In some instances, the length of the active area of a given elongated electrode ranges from 0.5 to 5 cm, such as 0.75 to 4 cm and including 1 to 2.5 cm. The width of the active area of a given electrode may also vary, and in some instances ranges from 0.1 to 2.5 cm, such as 0.25 to 1 cm and including 0.25 to 0.75 cm. In some instances, each of the first and second jaws comprises two or more elongated electrodes, such as three, four or five or more elongated electrodes. The number of elongated electrodes on each of the first and second jaws may be the same or different. The configuration of each elongated electrode may also vary, and therefore may be linear, curvilinear, angled, etc., as desired. Each of the elongated electrodes of the first and second jaws may be made up of any convenient material. Electrode materials of interest include, but are not limited to: platinum group metals, such as platinum, rhodium, palladium, rhenium, as well as tungsten, gold, silver, tantalum, and alloys of these metals; electrically conductive elastic materials, such as nickel/titanium alloys, copper/zinc alloys, or nickel/aluminum alloys; etc.

As reviewed above, in some instances at least one of first and second jaws has at least two elongated electrodes, wherein each of the first and second jaws may include two or more elongated electrodes, e.g., three or more, four or more, five or more, six or more, etc., elongated electrodes. The device may be configured to control the electrodes, e.g., control the polarity of the electrodes, in any desired fashion. For example, the polarity of each of the electrodes may be fixed and not changeable during operation. Alternatively, the device may be configured to independently control the polarity of one or more of the electrodes, including all of the electrodes. For example, the device may be configured to independently control the polarity of each of the electrodes, such that during use the operator may assign the desired polarity to each of the electrodes. In some instances, the elongated electrodes of each of the jaws are configured to have opposite polarity during use.

As summarized above, in addition to RF energy, the devices are configured to apply thermal ablative energy. While the thermal ablation energy component may vary, in some instances the thermal ablation energy component is made of one or more resistors fabricated from a positive temperature co-efficient of resistivity (i.e., PTC) material, e.g., where the PTC material may be present as a coating on the active surface of the resistor, or otherwise incorporated into the resistor. PTC materials of interest include semiconductor materials which exhibit a resistivity increase with increasing temperature, specifically an increase that is characterized by a slow increase in resistivity up to a the Curie temperature of the material. When a PTC material reaches its Curie temperature, the resistivity of the material increases by several orders of magnitude over a very small temperature range. Thus, the amount of current that can flow is very small compared to that which can flow at significantly lower temperatures. After this sharp rise, the resistivity approaches an almost constant value. As such, PTC materials of interest are those that first undergo a slow increase in resistance as the temperature increases. In the region of their characteristic Curie temperature, their resistivity increases dramatically over a very small temperature range. After this rapid increase, the resistivity approaches a maximum as the temperature rises further. PTC materials of interest include those having a Curie temperature ranging from 60 to 160° C., such as 75 to 150° C. and including 80 to 125° C. Materials exhibiting PTC properties include, but are not limited to: semiconducting titanate ceramics, such as but not limited to barium titanate, lead titanate and strontium titanate; ternary perovskites, e.g., $BaTiO_3$, and the like; etc., where these materials may include small amounts of dopants sufficient to provide for the desired semi-conductive property, where dopants of interest include, but are not limited to: trivalent ions (e.g., $Y^{3+}$, $La^{3+}$, $Nd^{3+}$, $Sm^{3+}$, etc.) and the like. Also of interest as PTC materials are PTC matrix materials, e.g., as described in U.S. Pat. Nos. 7,189,233; 7,196,146; 7,309,849; 7,381,209; and 7,981,113; the disclosures of which are herein incorporated by reference. In some instances, such PTC matrix materials are fabricated of a non-conductive polymer e.g., polypropylene or medical grade silicone polymer, that exhibits two phases that define greater and lesser conductive states. The first phase is a crystalline or semi-crystalline state where the polymer molecules form long chains and are arranged in a more ordered architecture. When the temperature of the material is elevated, the polymer molecules maintain the crystalline architecture or structure through a selected temperature range. The polymer is designed to transition to an at least partly amorphous phase from the crystalline state at a selected temperature range. In the amorphous state, the molecules are aligned more randomly, and there may be slight changes in material geometry at the macroscale. The non-conductive polymer is combined with a dispersed, highly conductive particles (e.g., carbon micro- or nanoparticles) to form a matrix. In the crystalline phase of the polymer, the carbon particles are packed into the crystalline boundaries and form many conductive paths across and through the matrix material. In this low temperature crystalline state, the polymer-carbon matrix is engineered to have a low resistance.

Where the thermal ablation energy component comprises a PTC resistor, the PTC resistor may have a variety of different configurations. The tissue contacting surface of the PTC resistor may vary as desired, e.g., depending on the number of distinct PTC resistors associated with the jaw, where the tissue contacting surface has, in some instances, an area ranging from 1 to 100 mm$^2$, such as 5 to 75 mm$^2$, including 15 to 45 mm$^2$. While the shape of the tissue contacting surface may vary, in some instances the tissue contacting surface has a rectilinear shape, e.g., a rectangular shape, including a square shape, where the dimensions of the rectilinear shape may vary, and in some width of the raised tissue contacting portion ranges from 2 to 10, e.g., 3 to 8, mm. While the number of PTC resistors making up a given thermal ablation energy component may vary, in some instances the thermal energy ablation element includes a single PTC resistor and in some instances includes a plurality, i.e., 2 or more, PTC resistors. When the thermal ablation energy component includes a plurality of PTC resistors, the number of resistors that make up the component may vary, ranging in some instances from 2 to 1000, such as 5 to 750, including 10 to 500, e.g., 50 to 250, including 75 to 125. Where the thermal energy component includes a plurality of PTC resistors, the resistors may assume a number of configurations, e.g., linear, curvilinear, etc. In some instances, the PTC resistors are arranged in linear fashion, e.g., along a least a portion of the length of the tissue contacting surface of the jaw. As desired, a given thermal ablation energy component may include a single linear arrangement of multiple PTC resistors, or two or more such linear arrangements, e.g., arranged in parallel. In a given jaw, the PTC resistor elements are operatively coupled to an electrical conductor(s). The PTC resistors may be coupled to the electrical conductor(s) in series or in parallel, as desired. In some instances, the PTC resistors are individually controllable in the jaw, such that each PTC resistor may be independently controlled relative to the other PTC resistors of the jaw. The device may be configured to control the resistors, e.g., control the temperature of the resistors, in any desired fashion. For example, the temperature of each of the resistors may be fixed and not changeable during operation. Alternatively, the device may be configured to independently control the temperature of one or more of the resistors, including all of the resistors. For example, the device may be configured to independently control the temperature of each of the resistors, such that during use the operator may assign the desired temperature to each of the resistors. Viewed another way, each PTC resistor of a collection of such resistors of a jaw may be individually addressable.

As indicated above, in some instances the jaw(s) are configured to apply both RF and thermal ablative energy to soft tissue. In such embodiments, the jaws may include an RF ablative energy element, e.g., an elongated electrode(s), and a PTC resistor element made up of one or more PTC resistors, e.g., in the form of one or more linear arrangements of PTC resistors. Where desired, these elements may be separated from either other by a spacer, i.e., a structure that is configured to separate the surface proximal RF ablation energy component and the surface distal thermal ablation element. The spacer may be configured to separate the two components by a desired distance, where this distance may vary, and in some instances ranges from to 0.01 to 10 mm, such as 0.1 to 5 mm. The separator may be made up of any convenient material, including rigid materials, e.g., glass epoxy, etc., and flexible materials, e.g., flexible polymeric, e.g., plastic, materials, such as polyimide, PEEK, polyester film, etc., and the like. In some instances the separator is made up of a flexible material, such that the combination of the RF and thermal ablation components and the separator may be referred to as a flex circuit.

While the RF and thermal ablation components of the jaws may be configured in a variety of different formats, in some instances each of the first and second jaws includes a flex circuit that is made up of: a flexible material having a tissue proximal side and a tissue distal side; a surface proximal RF ablation energy component present on the surface proximal side, wherein the RF ablation energy component comprises two elongated electrodes; and a surface distal thermal ablation energy component present on the surface distal side, wherein the surface distal thermal ablation energy component comprises two linear arrangements each made up of two or more PTC resistors. A schematic of the distal and proximal flex circuits of an embodiment of a device in accordance with the invention is provided in FIG. 1A. As shown in FIG. 1A, the distal flex circuit includes a PTC thermal ablation energy component and an RF ablation energy component, which components are present on opposites sides of a flexible separator material, e.g., as described above. The PTC thermal ablation energy component includes two linear arrangements of multiple PTC resistors operatively connected in parallel to positive and negative conductors flanking the linear arranges. The proximal flex circuit includes a similar arrangement of PTC resistors. Also shown for the distal flex circuit is a schematic of the RF ablation energy component, which component includes two elongated electrodes that are held at positive polarity. The proximal flex circuit includes an analogous RF ablation energy component that is made up of two elongated electrodes, where the electrodes are held at a negative polarity. As such, during use the electrodes of the proximal and distal flex circuits are at opposite polarity.

FIG. 1B provides a view of an alternative configuration for a flex circuit of the invention. As shown in FIG. 1B, two-side flex circuit 10 includes a first side, indicated side A, and a second side, indicated side B. Side A (i.e., the surface distal side when present in a jaw) displays first and second positive traces 11*a* and 11*b* flanking a central ground trace 12, which may be operably coupled to linear arrangements 13*a* and 13*b* of multiple PTC resistors in parallel, as shown, to provide for the desired linear arranging 520 of the PTC resistors 509 in the ablation element 500. Side B (i.e., the surface proximal side when present in a jaw) of flex circuit 10 includes RF electrodes 14a and 14b.

Figure 2B:
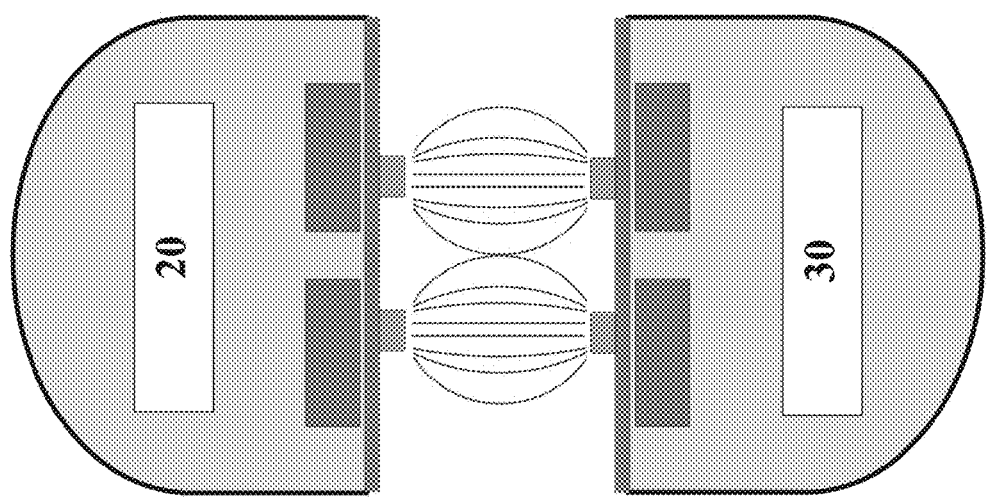
Figure 2C:
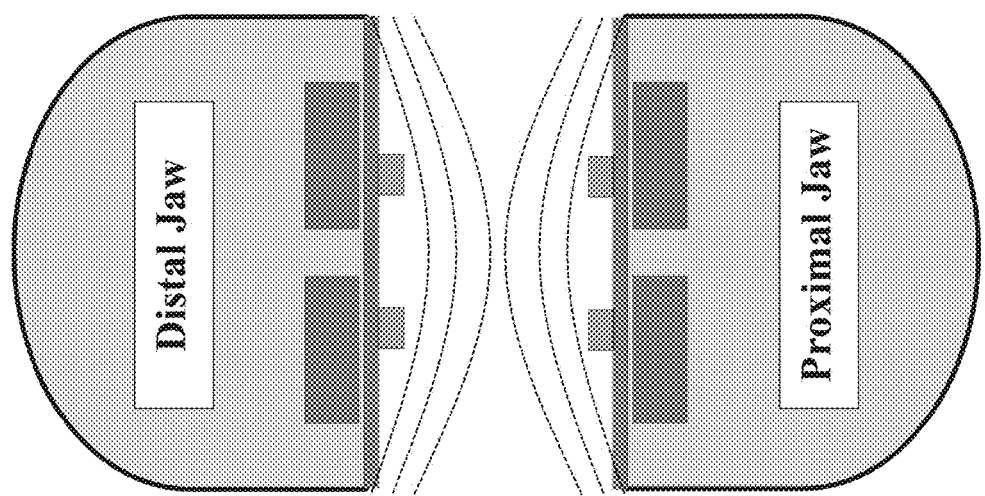
Figure 2D:
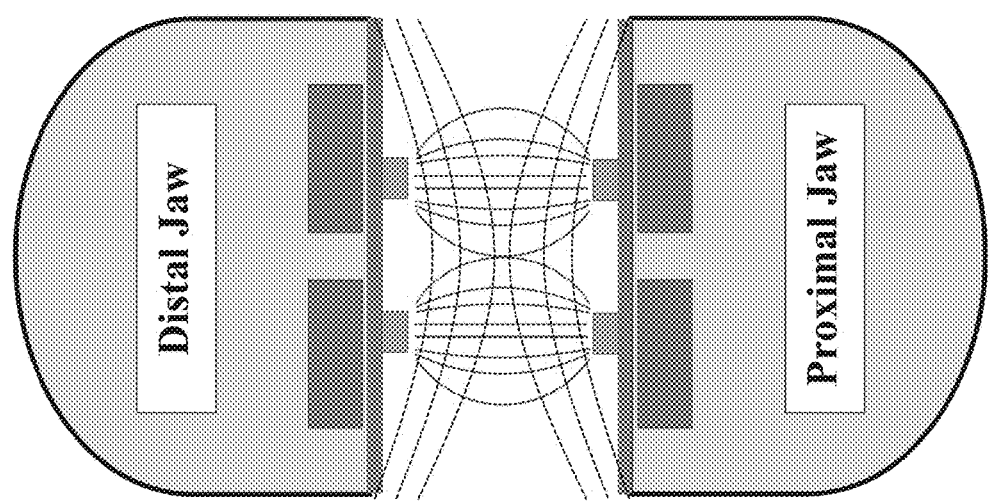

FIG. 2A provides a cross-sectional view of proximal and distal jaws according to an embodiment of the invention, where the jaws include the proximal and distal flex circuits schematically shown in FIG. 1A. As shown in FIG. 1B, both distal jaw 20 and proximal jaw 30 include an surface proximal RF ablation energy component 40 made up of first and second elongated electrodes 42 and 44, and a surface distal thermal energy component 50 made up of two linear arrangements of multiple PTC resistors, 52 and 54. FIG. 2B shows the device of FIG. 2A, where the RF electrodes are energized, which provides for inter ablative energy to be applied to tissue positioned between the jaws. FIG. 2C shows the device of FIG. 2A, where the PTC elements are energized, which provides for intra ablative energy to be applied to tissue positioned between the jaws. FIG. 2C shows the device of FIG. 2A, where both the RF electrodes and the PTC elements are energized, which provides for inter and intra ablative energy to simultaneously be applied to tissue positioned between the jaws.

In tissue ablation devices of the invention, the jaws may be configured in any desirable manner. As such, the jaws may be planar, curved, or have more complex configurations. In some instances, the first and second jaws are multi-dimensional curved jaws. By "multi-dimensional curved jaws" is meant that the jaws have a curve that may be described as having different components each of which may be defined by a different two-dimensional plane. For example, multi-dimensional curved jaws of the devices described herein may have a curve which can be defined as having a first curvature component which may be defined in a first two-dimensional plane and a second curvature component which may be defined in a second two-dimensional plane. Viewed another way, the first and second jaws may be curved in a manner such that they simultaneously define a first curve in a first plane, e.g., an X-Y plane, and a second curve in a second plane, e.g., an X-Z plane. As such, the first and second jaws are, in some instances, jaws which are curved in two planes. The radius of curvature of the curves of the first and second jaws may vary, and ranges in some instances from 1 to 30 cm, such as 2 to 25 cm. As the first and second jaws are multi-dimensional curved jaws, the long axis of the jaws extends through three-dimensional space. It is noted that while multi-dimensional curved jaws are described in connection with the RF and thermal ablation energy components such as described above, they are not limited to be used with such. Accordingly, aspects of the invention include tissue ablation devices having multi-dimensional curved jaw having any other desired ablation energy component, including but not limited to just RF components, just thermal components, just cryo components, etc.

The first and second jaws may assume a variety of different configurations. In some instances, at least one of the first and second jaws is collapsible into the elongated member. By "collapsible into the elongated member" is meant that at least one of the jaws, e.g., the jaw closest to the proximal end, may be folded at least partially into a receiving space, such as a cavity, in the elongated member, for example so that the device has a lower profile during introduction into a body, e.g., prior to deployment and use. In some instances, each of the first and second jaws may be collapsible into the elongated member. Where one or both of the jaws is collapsible into the elongate body, any convenient mechanism may be employed for moving the jaw(s) from the collapsed to deployed state (the latter being employed during application of ablative energy to target tissue). For example, one or both of the jaws may be attached to the elongated member via a hinge, and a spring or other force applying mechanism may be employed to assist in transitioning the jaw(s) from the collapsed to deployed state, as desired. Where desired, one of the jaws, e.g., the distal jaw, may be fixed relative to the elongated member of the device, such that it is not moveable relative to the elongated member. Embodiments of such devices include those where the proximal jaw is collapsible and the distal jaw is fixed.

Whether the jaws are collapsible or not, in some instances the first and second jaws are configured to assume a parallel configuration prior to contacting tissue in ablative energy engagement, e.g., prior to clamping and then ablating tissue. As such, prior to tissue engagement, the first and second jaws may be configured to assume a parallel configuration with one another, e.g., where the tissue contact surfaces are in opposing relationship (i.e., facing each other) and the distance between the opposing tissue contact surfaces does not substantially change along the lengths of the electrodes, e.g., where the magnitude of any change is 5 mm or less, such as 2.5 mm or less, including 1 mm or less. In yet other embodiments, the first and second jaws may be configured to assume a non-parallel opposing configuration prior to engaging, e.g., clamping, tissue. In such instances, the distance between the opposing tissue contact surfaces may substantially change along the lengths of the electrodes, e.g., where the magnitude of any change is 7.5 mm or more, such as 10 mm or more, including 15 mm or more.

In some instances, the first and second jaws are configured to not exceed a compressive force limit on tissue positioned between the jaws during use. In other words, the first and second jaws are configured so that the compressive force applied to tissue engaged by the jaws during application of ablative energy does not exceed a predetermined threshold or limit, i.e., compressive force limit. While the compressive force limit may vary, in some instances the compressive force limit is one that does not result in unwanted tissue damage. While the compressive force limit for a given device may vary, in some instances it is a force resulting from a constant force spring, e.g., a constant force spring configured to apply a force of 3 to 20, such as 5 to 15, e.g., 7.5 to 10 lbsf/in. Any convenient mechanism may be employed to provide for this configuration. In some instances, the device comprises a spring mechanism configured to limit the compressive force applied to tissue positioned between the jaws during use, e.g., as described in greater detail below.

Where desired, one of the first and second jaws, such as the jaw most distal from the proximal end of the device, may include an illumination element. Any convenient illumination element may be employed that provides light of one or more wavelengths, such as in the visible range. As such, the illumination element may provide white light or light in a particular wavelength range. The illumination element may vary, where illumination elements of interest include light emitting diodes (LEDs), incandescent bulbs, and the like. The illumination element, when present, may be positioned at any convenient location on the jaw, e.g., at or near the distal end of the jaw (i.e., that end of the jaw furthest away from the elongated member). The illumination element may be configured to be always on during use, or controllable so that it can be turned on and off during a procedure, as desired.

As summarized above, in addition to the first and second jaws at the distal end, the ablation devices described herein further include a connector at the proximal end for operatively connecting to an ablation energy source. Any convenient connection element may be employed. Also present at the proximal end may be one or more actuators, e.g., for deploying the jaw(s), for engaging tissue, for operating the electrodes, for operating the illumination element, for manipulating the distal end of the device, etc. In some instances, the proximal end includes handle that includes finger grips, a compression actuator for moving the first and second jaws towards each other, and a release lever.

In some instances, the ablation device is configured to be handheld. While the weight of the devices may vary, in some instances the weight of the devices is 3 lbs. or less, such as 2 lbs or less, and including 1 lb. or less, ranging in some instances from 0.25 to 3 lbs, such as 0.50 to 2 lbs.

The ablation devices may include a number of additional elements, as desired. For example, the ablation devices may include a temperature control element, e.g., cooling element, heat sink, etc., a sensor electrode, a pacing electrode, etc.

Figure 3A:
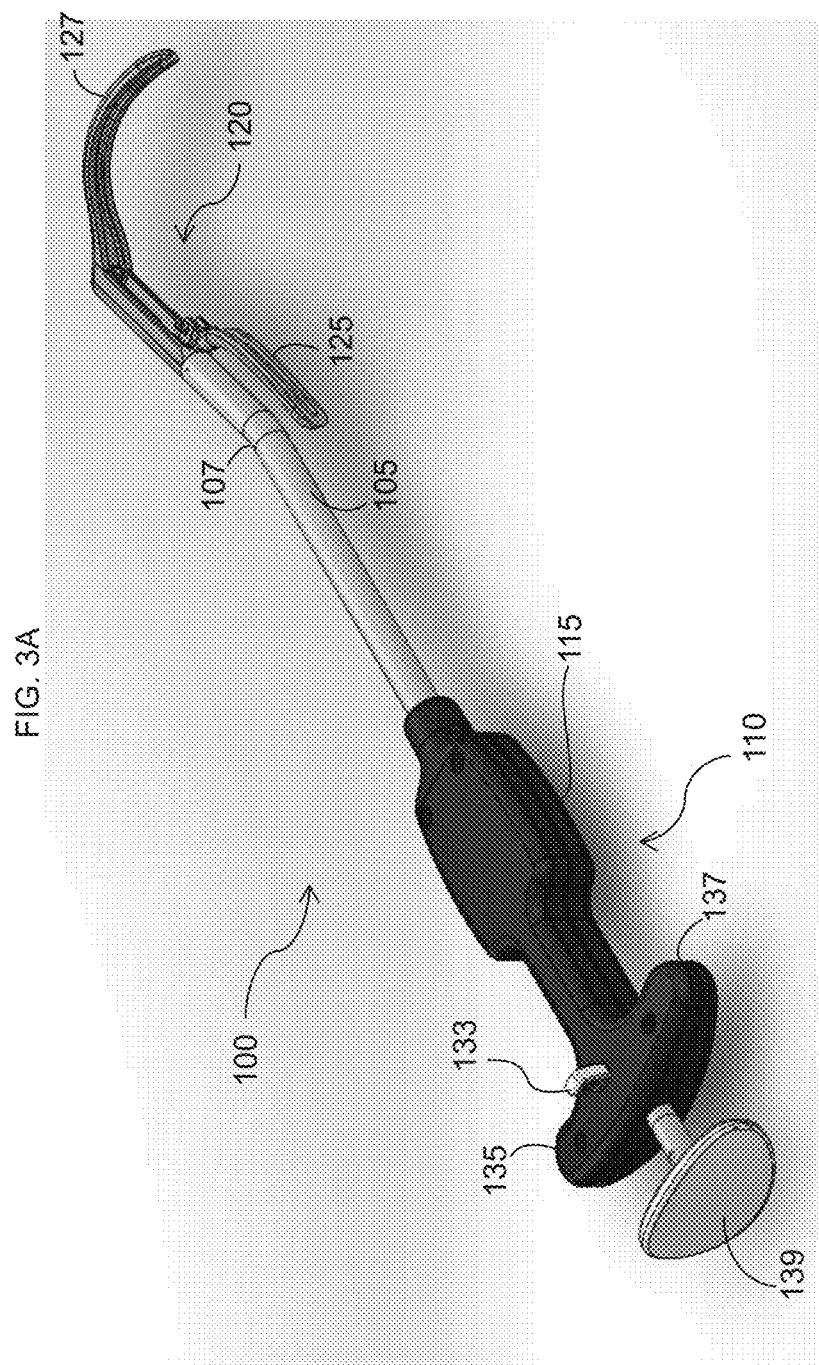
FIGS. 3A and 3B provide views of an ablation device in an un-deployed and deployed state, respectively, in accordance with an embodiment of the invention.
Figure 3B:
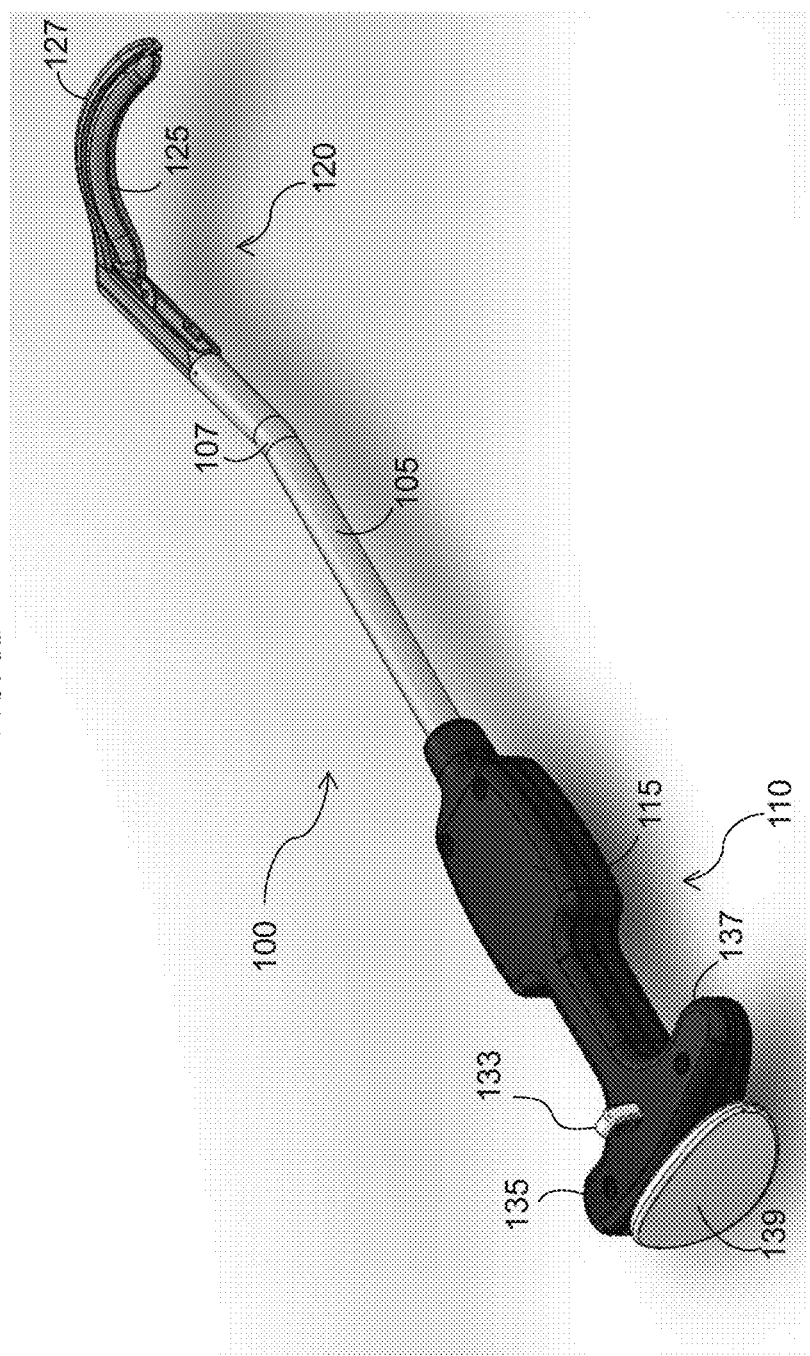

An example of a tissue ablation device according to an embodiment of the invention is illustrated in FIGS. 3A and 3B. FIG. 3A provides a three-dimensional view of the device as viewed from the proximal to distal end where the device is in an "open" configuration. FIG. 3B provides a three-dimensional view of the device as viewed from the proximal to distal end where the device is in a "closed" configuration. In FIG. 3A, device 100 includes an elongated body 105 positioned between a handle 115 located at the proximal end 110 and first and second jaws 125 and 127 located at the distal end 120. Elongated body 105 is a rigid tubular structure made of a metal, e.g., stainless steel, and having an outer diameter of ranging from 5 to 20 mm and an inner diameter ranging of 2.5 to 17.5 mm. The space defined inside the elongated body 105 houses various connectors and actuators that operably connect the jaws at the distal end to the handle 115 at the proximal end. Also shown is bend 107 which has an angle that is 15°. As summarized above, first and second jaws 125 and 127 are in an open configuration, where jaw 125 (which may be identified as the proximal jaw) is folded back onto elongated body 105 to provide for ease of deployment to a target tissue site. Handle 115 includes first and second finger grips 135 and 137, as well as actuator 139 which is pushed towards the distal end to move the jaws from the open to closed position and release lever 133 which is can be moved to a release position to move the jaws back to an open position following an ablation procedure. FIG. 3B shows the device in FIG. 3A, where jaws 125 and 127 (i.e., proximal and distal jaws respectively) are in a closed position. As can be seen in FIG. 3B, actuator 139 has been pressed into handle 115. As can be seen in FIGS. 3A and 3B, jaws 125 and 127 are multi-dimensional curved jaws, in that each jaw curves in a first plane that is shared by the long axis of the device and also in a second plane that is orthogonal to the first plane at the distal end of the device.

FIGS. 4A to 4C provide various views of the proximal and distal jaws of the device 100 of FIGS. 3A and 3B. FIGS. 4A and 4B provide two different views of the jaws 125 and 127 in an open configuration. As shown, proximal jaw 125 is folded back and away from distal jaw 127. Distal jaw 127 includes track 210 along which proximal jaw 125 can slide when moving between the open and closed positions. Also shown is hinge 215 of proximal jaw 125. FIG. 4C provides a three dimensional view of the proximal and distal jaws 125 and 127 in a closed configuration. As shown in FIG. 4C, proximal jaw 125 has been moved along track 210 towards distal jaw 127 and moved from the folded back position to a deployed position. The space 225 between the proximal and distal jaws 125 and 127 is uniform along the length of the jaws extending from position 235 to 237. While the width of this uniform space may vary, in some instances this width ranges from 1 to 20, such as 2 to 10 mm.

FIG. 5A provides a view of the distal jaw housing 300 of distal jaw 127. As shown in FIG. 5A, distal jaw housing includes track 210 and fixed multi-dimensional jaw case 305. Also shown is space 315 that is configured to receive an ablation element, which ablation element may include RF and/or thermal ablative elements and supporting circuitry, e.g., the form of a flex circuit, such as described above. FIG. 5B provides a top view of multi-dimensional jaw case 305. As illustrated, multi-dimensional jaw case 305 curves in the plane of the page as well as in the plane extending up from the surface of the page.

FIGS. 6A and 6B provide side and top views, respectively, of proximal jaw 125. As shown in FIG. 6A, jaw 125 is also a multi-dimensional curved jaw, which curves in a manner that corresponds to or matches the curve of the distal jaw shown in FIGS. 5A and 5B, such that a uniform working space is defined between the jaws when the jaws are deployed in the closed position.

FIGS. 7A and 7B provide views of handle 115 present at the proximal end of the device shown in FIGS. 3A and 3B. FIG. 7A provides a view of handle 115 in the non-deployed position, i.e., when the jaws are in the open configuration. As shown, handle 115 includes actuator 139 which is extended from the handle itself by distance d, which distance d may vary and in some instances ranges from 10 to 50 mm. Also shown is release lever 133. FIG. 7B shows the handle 115 after deployment of the jaws by moving actuator 139 into handle 115. To deploy the device, an operator may grasp the handle by the finger grips with the fore and middle finders, and then depress the actuator into the handle with the palm.

Figure 9:
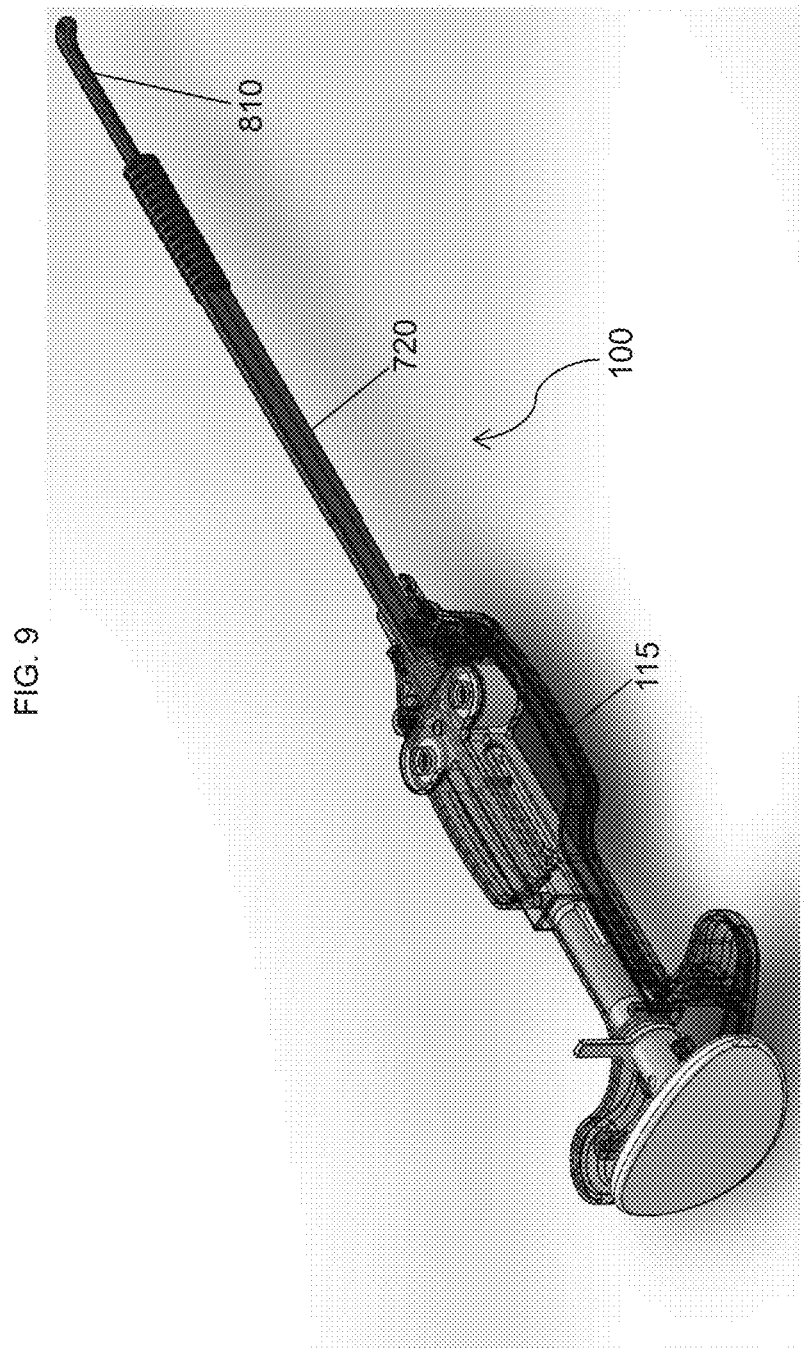
FIG. 9 provides a view the handle shown in FIGS. 8A and 8B, as well as the distal end of the jaw actuator.

FIGS. 8A and 8B provide cutaway views of the handle 115 in the un-deployed and deployed states, respectively. In FIG. 8A, handle 17 includes actuator 139 which has plunger rod 710 extending into the handle. At the distal end of the plunger rod 710 is jaw actuator 720. Actuator 139 is maintained in the non-deployed state by spring 725, which is present in the uncompressed state. Coupled to spring 725 are constant force springs 705 and 707 which are configured to ensure that, during deployment, the jaws exert a constant predetermined force on tissue positioned therebetween. While this constant force may vary, in some instances it ranges from 5 to 15, e.g., 7.5 to 10. Also shown is release lever 133. In FIG. 8B, the jaws have been deployed by moving actuator 139 into handle 115, e.g., as described above. Movement of actuator 139 into handle 115 moves plunger rod 710 towards the distal end of the device, and, in turn, moves jaw actuator 720 towards the distal end of the device. Movement of the plunger rod 710 towards the distal end also compresses spring 725 and simultaneously unwinds springs 705 and 707, which results in a constant compressive force on target tissue positioned between jaws at the distal end, e.g., as described above. Release lever 133 in combination with release spring 730 prevents the actuator from moving backwards out of the handle during the ablation procedure, i.e., it stabilizes the actuator and therefore the jaws in the deployed or closed configuration during ablation. Following an ablation procedure, release lever 133 may be manually moved toward the proximal end of handle 115 as shown in FIG. 8A to release the actuator and therefor the jaws at the distal end, so that the jaws may assume an open configuration. The handle and components thereof may be fabricated from any convenient material, including polymeric materials, e.g., plastics such as ABS or polycarbonate, metals, e.g., stainless steel, and the like FIG. 9 provides another view of device 100 showing distal end 810 of jaw actuator 720, which distal end 810 is configured to operably mate with proximal jaw 125 (not shown) and thereby move proximal jaw towards distal jaw 127 during deployment and ablation.

During use, the devices described herein may be operatively connected to an ablation energy source. Any convenient ablation energy source may be operatively connected to the device, e.g., via the proximal end connector. Examples of suitable energy sources or generators include, but are not limited to, those described in U.S. Pat. Nos. 8,585,694 and 6,235,022, the disclosures of which are herein incorporated by reference.

Methods

Aspects of the invention include methods of ablating tissue with the tissue ablation devices, e.g., as described above. Such methods may include positioning target tissue (e.g., soft tissue) between the first and second jaws and then engaging the target tissue with the jaws, e.g., by deploying the jaws into a clamped position about the tissue. As described above, at least one of the first and second jaws may be collapsible relative to the elongated member, e.g., to provide for easier access of the jaws to the target tissue. In such instances, the methods may include positioning the distal end of the elongated member in the vicinity or area of the target tissue and then deploying the collapsed jaw, followed by engagement of the target tissue between the first and second jaws.

Following engagement of the target tissue between the first and second jaws, aspects of the methods include applying ablative energy to the tissue disposed between the first and second jaws to ablate the tissue, e.g., as described above. As discussed above, the applied ablative energy may be RF and/or thermal ablative energy. Where desired, prior to application of ablative energy, the method may include independently controlling each of the ablative elements of the jaws, e.g., the elongated electrodes and/or one or more PTC resistors. For example, where each of the first and second jaws includes a flex circuit, e.g., as described above, the methods may include independently selecting the polarity of the RF electrodes and temperature of the various PTC resistors of the linear arrangements so as to provide for desired ablation of engaged tissue. In a given procedure, ablative energy may be applied via the ablative element(s) of the jaws for a desired period of time, where in some instances the period of time ranges from 5 to 120 seconds, such as 15 to 90 seconds, e.g., 30 to 60 seconds. During a given procedure, ablative energy may be applied a single time or multiple times in which each time is separated by an intervening period of time in which no ablative energy is applied. When present, this intervening period may vary in length, ranging in some instances from 1 to 10, such as 1 to 5 s.

As described above, some embodiments of the devices include an illumination element associated with one of the first and second jaws. In such instances, the methods may include detecting light from the illumination element, e.g., by visually detecting the light, detecting the light with a detector, etc. Information from such detection may be employed, as desired, to guide the surgical procedure in which the device is being element, e.g., to guide the correct placement of the distal end of the device in the vicinity of the target tissue, etc.

The target tissue may, in some instances, be part of a living subject or animal. The term "subject" is used interchangeably herein with the term "patient". In certain embodiments, a subject is a "mammal" or a "mammalian" subject, where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the subject is a human. The term "humans" may include human subjects of both genders and at any stage of development (e.g., fetal, neonates, infant, juvenile, adolescent, and adult), where in certain embodiments the human subject is a juvenile, adolescent or adult. While the methods described herein may be applied to perform a cardiac surgical procedure on a human subject, it is to be understood that the subject methods may also be carried out to perform a cardiac surgical procedure on other subjects (that is, on "non-human subjects").

A variety of different target tissues may be ablated with devices as described herein. Examples of different types of tissues and applications with which the devices described herein may be employed include those described in the Introduction section, above. Types of tissues include, but are not limited to, uterine tissue, vascular structures, e.g., varicose veins, renal arteries, tumors, and cardiac tissue.

In some versions of the disclosed methods, the method is a surgical procedure. As used herein, the phrase "surgical procedure" refers to a procedure (e.g., a medical procedure) involving at least one incision in the body of a subject and/or performed using one or more instruments (e.g., surgical instruments). A surgical procedure may be carried out through a body cavity and/or through the skin of a subject.

As noted above, in certain variations of the disclosed methods, the method is an open surgical procedure. As used herein, the phrase "open surgical procedure" refers to a surgical procedure wherein at least one long incision (e.g., having a length of 10 cm) is made in the body of a subject to introduce at least one surgical instrument and/or visualize the surgery through the incision. In an open surgical procedure, closure devices, e.g., staples, sutures, etc., may be used to close at least one incision.

In certain variations of the disclosed methods, the method is a minimally invasive surgical procedure. As used herein, the phrase "minimally invasive surgical procedure" refers to a surgical procedure that is less invasive than an open surgical procedure. A minimally invasive surgical procedure may involve the use of arthroscopic and/or laparoscopic devices and/or remote-control manipulation of surgical instruments. Minimally invasive surgical procedures include endovascular procedures, which may be totally endovascular procedures, percutaneous endovascular procedures, etc. Endovascular procedures are procedures in which at least a portion of the procedure is carried out using vascular access, e.g., arterial access.

Utility

The devices and methods of the invention, e.g., as described above, find use in a variety of different applications, e.g., applications where ablation of target tissue (such as of a living animal) is desired. Examples of such applications include, but are not limited to, treatment of tumors, e.g., tumors of the liver, treatment of hypertension, e.g., through ablation of renal nerves, treatment of uterine bleeding, and treatment of cardiac conditions, e.g., to treat or prevent atrial fibrillation.

By treatment is meant that at least an amelioration of the symptoms associated with the condition afflicting the subject is achieved, where amelioration is used in a broad sense to refer to at least a reduction in the magnitude of a parameter, e.g. symptom, associated with the condition being treated. As such, treatment also includes situations where the condition, or at least symptoms associated therewith, are completely inhibited, e.g. prevented from happening, or stopped, e.g. terminated, such that the subject no longer suffers from the condition, or at least the symptoms that characterize the condition. In certain embodiments, the condition being treated is a disease condition.

One application of interest in which ablation devices described herein find use is in pulmonary vein isolation. The pulmonary veins return oxygenated blood from the lungs to the left atrium. There are typically four pulmonary veins, a superior pulmonary vein and an inferior pulmonary vein from each lung. On the right side of the heart, the superior pulmonary vein passes posterior to the superior vena cava, the inferior behind the right atrium. On the left side of the heart, both the superior and inferior pulmonary veins pass anterior to the descending thoracic aorta.

By "pulmonary vein isolation" is meant a partial or complete electrical isolation of one, two, three, or four pulmonary veins from the left atrium of the heart. Electrical isolation may be achieved using a RF ablative device (e.g., as described herein) to ablate a target tissue of interest. By "ablative" or "ablate" is meant the removal or alteration of electrically-conducting tissue in a target area of interest (e.g., a circumferential ablation region surrounding a pulmonary vein ostium, or two or more (e.g., each) of the four pulmonary vein ostia), such that the tissue no longer conducts or generates an electrical impulse sufficient to generate or propagate an arrhythmia. The process of ablation can prevent an arrhythmia from developing because the tissue that provides a trigger for an arrhythmia has been destroyed. The process of ablation can also prevent an arrhythmia from propagating to other areas of the heart by the creation of a line, or lesion, which electrically isolates the tissue and blocks passage of the electrical impulse. Ablation "lines" or "lesions" can be focal areas which are separate from other areas of ablation, or they can be contiguous, such they form lines or lesions connected to each other, which can form, for example, a continuous line, or ring, or circle, in order to electrically isolate the pulmonary vein(s).

In some embodiments, ablation can be performed by directly contacting a portion of cardiac tissue with an ablative device in a manner sufficient to create a lesion. For example, in some embodiments, an ablation device can be located sufficiently close to an area of cardiac tissue of interest, such that radiofrequency energy is delivered to the cardiac tissue in a manner sufficient to create a lesion. In some embodiments, the ablation is transmural, i.e., extends through the entire heart wall. In other embodiments, the ablation does not extend through the entire thickness of the cardiac wall; however, the degree of ablation may be sufficient to block electrical conduction.

The ablative device may be contacted with a portion of cardiac tissue to form a lesion. The methods can further include repeating the contacting and ablating a number of times to produce a plurality of lesions. For example, the contacting step may be performed two or more times, such as three or more, or four or more times, etc. In some embodiments, the contacting and ablating step is performed in the same location.

In some embodiments, the contacting and ablating step can be performed in overlapping locations, such that part of a second location overlaps with part of a first ablating location, such as in the case of creating a continuous linear ablation line. In other embodiments, a second ablation step may be in a different location from the first ablation step, e.g. to create circumferential lesions around the connection area between a pulmonary vein and the left atrium.

As summarized above, the pulmonary vein isolation may be performed using an ablative surgical device, e.g., as described above. An ablative surgical device of the subject methods can be in the shape of a clamp, with an upper and a lower jaw, such that the ablation device is a clamping device. In other embodiments, the ablative device can have an elongated cylindrical shape, such as that of a pen. In some embodiments, the ablation device can have a linear shape, a rectangular shape, a semi-circular shape, an "L" shape, a "U" shape, or any other suitable shape. The configuration of the surface of the ablation device that contacts the tissue can also be any suitable two-dimensional shape such as a line, a square, an oval, a triangle, etc. In some embodiments, the ablation device can further employ suction to pull tissue into the device.

Where the devices described herein are RF devices, they deliver radiofrequency energy to a target tissue of interest. The heat generated by the RF energy ablates the tissue, resulting in the formation of scar tissue at the ablation site. As described above, the radiofrequency ablative surgical device is a multielectrode (e.g., "multipolar") radiofrequency ablative surgical device, e.g., a device which transmits RF energy from two or more electrodes (e.g., 2, 3, 4, 5, 6, 7, 8, or more electrodes). When the subject methods employ a multielectrode radiofrequency ablative surgical device, the device may be a bipolar or quadripolar ablative surgical device. The terms "bipolar" and "quadripolar" indicate that the ablation path extends locally between two or four electrodes (respectively) in the device, rather than between one electrode and a general remote, or external electrode. Such devices may be configured to deliver ablation energy to achieve a uniform, superficial depth of ablation between ~500 μm and ~1,000 μm.

Cardiac applications in which the subject devices and methods find use further include those applications described in U.S. Pat. No. 8,617,145; the disclosure of which is herein incorporated by reference.

The disclosed devices and methods perform ablation protocols in a time-efficient manner. More specifically, by using the subject devices and methods, the total time that an ablation procedure takes can be reduced. The time of such a procedure can be reduced by eliminating or reducing the time required for applying ablative energy multiple times to tissue. A reduced time for a surgical process can help prevent fatigue in attending medical staff and can otherwise reduce risk to the patient. For example, a pulmonary vein isolation procedure as described above may be performed with the subject devices in a period of time ranging from 0.5 to 5 min, such as 0.5 to 2 min, including 0.5 to 1 min, which is substantially shorter than the time required using other ablative, e.g., RF, devices.

Kits

Also provided are kits that at least include the subject devices and which may be used according to the subject methods. The subject kits at least include an ablation device, e.g., as described above. The kits may further include one or more components to be employed in a given surgical procedure, e.g., trocars, tissue dissectors, etc., e.g., as described in greater detail below, and the like. The components of the kits may be present in sterile packaging, as desired.

In certain embodiments, the kits which are disclosed herein include instructions, such as instructions for using devices. The instructions for using devices are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging etc.). In other embodiments, the instructions are present as an electronic storage data file present on a suitable computer readable storage medium, e.g., Portable Flash drive, CD-ROM, diskette, etc. The instructions may take any form, including complete instructions for how to use the device or as a website address with which instructions posted on the world wide web may be accessed.

In addition, embodiments of the disclosed kits or their components may be used according to any of the embodiments of the methods described herein or combinations thereof.

Notwithstanding the appended clauses, the disclosure is also defined by the following clauses:

1. A tissue ablation device, the device comprising:
    an elongated member having a proximal and distal end;
    first and second jaws at the distal end that are configured to apply ablation energy to tissue disposed between the jaws during use, wherein each jaw comprises a surface proximal radiofrequency (RF) ablation energy component and a surface distal thermal ablation energy component; and
    a connector at the proximal end for operatively connecting to an ablation energy source.
2. The tissue ablation device according to Clause 1, wherein the RF ablation energy component comprises one or more elongated electrodes.
3. The tissue ablation device according to Clause 2, wherein RF ablation energy component comprises two elongated electrodes.
4. The tissue ablation device according to Clause 3, wherein the elongated electrodes of each of the jaws are configured to have opposite polarity during use.
5. The tissue ablation device according to any of the preceding clauses, wherein thermal ablation energy component comprises a positive temperature co-efficient of resistivity (PTC) material.
6. The tissue ablation device according to Clause 5, wherein the thermal ablation energy component comprises a linear arrangement of two or more PTC resistors.
7. The tissue ablation device according to Clause 6, wherein the thermal ablation energy component comprises two linear arrangements each made up of two or more PTC resistors.
8. The tissue ablation device according to any of Clauses 6 and 7, wherein the linear arrangement comprises 2 to 1000 PTC resistors.
9. The tissue ablation device according to any of Clauses 6 to 8, wherein the PTC resistors are connected in series.
10. The tissue ablation device according to any of Clauses 6 to 8, wherein the PTC resistors are connected in parallel.
11. The tissue ablation device according to any of the preceding clauses, wherein the surface proximal RF ablation energy component and a surface distal thermal ablation energy component are separated from each other by a separator.
12. The tissue ablation device according to Clause 11, wherein the separator comprises a flexible material.
13. The tissue ablation device according to Clause 12, wherein each of the first and second jaws comprises a flex circuit comprising:
    a flexible material having a tissue proximal side and a tissue distal side;
    a surface proximal RF ablation energy component present on the surface proximal side, wherein the RF ablation energy component comprises two elongated electrodes; and
    a surface distal thermal ablation energy component present on the surface distal side, wherein the surface distal thermal ablation energy component comprises two linear arrangements each made up of two or more PTC resistors.
14. The tissue ablation device according to any of the preceding clauses, wherein each of the first and second jaws is a multi-dimensional curved jaw.
15. The tissue ablation device according to Clause 14, wherein the multi-dimensional curved jaws are curved in two planes.
16. The tissue ablation device according to any of the preceding clauses, wherein at least one of the first and second jaws is collapsible into the elongated member.
17. The tissue ablation device according to any of the preceding clauses, wherein the first and second jaws are configured to not exceed a predetermined compressive force limit on tissue positioned between the jaws during use.
18. The tissue ablation device according to Clause 17, wherein the device comprises a constant force spring mechanism configured to limit the compressive force applied to tissue positioned between the jaws during use.
19. The tissue ablation device according to any of the preceding clauses, wherein the elongated member is rigid.
20. The tissue ablation device according to Clause 19, wherein the rigid elongated member comprises a bend.
21. The tissue ablation device according to any of the preceding clauses, wherein at least one of the first and second jaws comprises an illumination element.
22. The tissue ablation device according to Clause 21, wherein the illumination element comprises an LED.
23. The tissue ablation device according to any of the preceding clauses, wherein the device comprises a handle at the proximal end.
24. The tissue ablation device according to Clause 23, wherein the handle comprises finger grips, a compression actuator for moving the first and second jaws towards each other, and a release lever.
25. An ablation system comprising:
    a tissue ablation device according to any of Clauses 1 to 24 operatively connected to an ablation energy source.
26. A method of ablating tissue, the method comprising:
    positioning the tissue between first and second jaws of an tissue ablation device according to any of Clauses 1 to 24, wherein the tissue ablation device is operatively coupled to an ablation energy source; and
    applying ablation energy to the tissue disposed between the first and second jaws to ablate the tissue.
27. The method according to Clause 26, wherein the tissue is part of a living animal.
28. The method according to Clause 27, wherein the tissue is cardiac tissue.
29. The method according to any of Clauses 26 to 28, wherein the method is an open surgical procedure.
30. The method according to any of Clauses 26 to 28, wherein the method is a minimally invasive surgical procedure.
31. The method according to any of Clauses 26 to 30, wherein the at least one of the first and second jaws comprises an illumination element and the method comprises detecting light from the illumination element.

32. A kit comprising:
   a tissue ablation device according to any of Clauses 1 to 24; and
   sterile packaging, wherein the tissue ablation device is present in the sterile packaging.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A tissue ablation device, the device comprising:
   an elongated member having a proximal and distal end;
   first and second jaws at the distal end that are configured to apply ablation energy to tissue disposed between the jaws during use;
   the first jaw comprising a first surface proximal radiofrequency (RF) ablation energy component and a first surface distal thermal ablation energy component;
   a first separator of a flexible material configured to separate the first surface proximal RF ablation energy component of the first jaw from the first surface distal thermal ablation energy component of the first jaw;
   the second jaw comprising a second surface proximal RF ablation energy component and a second surface distal thermal ablation energy component;
   a second separator of a flexible material configured to separate the second surface proximal RF ablation energy component of the second jaw from the second surface distal thermal ablation energy component of the second jaw; and
   a connector at the proximal end for operatively connecting to an ablation energy source.

2. The tissue ablation device according to claim 1, wherein each of the first surface proximal RF ablation energy component and the second surface proximal RF ablation energy component comprises one or more elongated electrodes.

3. The tissue ablation device according to claim 2, wherein the first surface proximal RF ablation energy component comprises two elongated electrodes, and the second surface proximal RF ablation energy component comprises two other elongated electrodes.

4. The tissue ablation device according to claim 3, wherein the elongated electrodes of each of the jaws are configured to have opposite polarity during use.

5. The tissue ablation device according to claim 1, wherein each of the first surface distal thermal ablation energy component and the second surface distal thermal ablation energy component comprises a positive temperature co-efficient of resistivity (PTC) material.

6. The tissue ablation device according to claim 5, wherein each of the first surface distal thermal ablation energy component and the second surface distal thermal ablation component comprises a linear arrangement of two or more PTC resistors.

7. The tissue ablation device according to claim 1, wherein the first jaw comprises a first flex circuit comprising:
   the first separator that is a flexible material having a tissue proximal side and a tissue distal side;
   the first surface proximal RF ablation energy component present on the tissue proximal side of the first separator, wherein the first surface proximal RF ablation energy component comprises two elongated electrodes;
   the first surface distal thermal ablation energy component present on the tissue distal side of the first separator, wherein the first surface distal thermal ablation energy component comprises two linear arrangements each made up of two or more PTC resistors; and
   the second jaw comprises a second flex circuit comprising:
   the second separator that is a flexible material having a tissue proximal side and a tissue distal side;
   the second surface proximal RF ablation energy component present on the tissue proximal side of the second separator, wherein the second surface proximal RF ablation energy component comprises two elongated electrodes; and
   the second surface distal thermal ablation energy component present on the tissue distal side of the second separator, wherein the second surface distal thermal ablation energy component comprises two linear arrangements each made up of two or more other PTC resistors.

8. The tissue ablation device according to claim 1, wherein each of the first and second jaws is a multi-dimensional curved jaw.

9. The tissue ablation device according to claim 8, wherein the multi-dimensional curved jaws are curved in two planes.

10. The tissue ablation device according to claim 1, wherein at least one of the first and second jaws is collapsible into the elongated member.

11. The tissue ablation device according to claim 1, wherein the first and second jaws are configured to not exceed a predetermined compressive force limit on tissue positioned between the jaws during use.

12. The tissue ablation device according to claim 11, wherein the device comprises a constant force spring mechanism configured to limit the compressive force applied to tissue positioned between the jaws during use.

13. The tissue ablation device according to claim 1, wherein the elongated member is rigid.

14. The tissue ablation device according to claim 13, wherein the rigid elongated member comprises a bend.

15. The tissue ablation device according to claim 1, wherein at least one of the first and second jaws comprises an illumination element.

16. The tissue ablation device according to claim 1, wherein the device comprises a handle at the proximal end.

17. An ablation system comprising: the tissue ablation device according to claim 1 operatively connected to the ablation energy source.

18. A method of ablating tissue, the method comprising: positioning the tissue between the first and second jaws of the tissue ablation device according to claim 1, wherein the tissue ablation device is operatively coupled to the ablation energy source; and applying ablation energy to the tissue disposed between the first and second jaws to ablate the tissue.

* * * * *